United States Patent
Fan et al.

(10) Patent No.: US 7,901,922 B2
(45) Date of Patent: Mar. 8, 2011

(54) NUTRIENT MEDIUM USED FOR EX VITRO SOWING, GERMINATION, GROWTH AND CONVERSION OF PLANT SOMATIC EMBRYOS OR GERMINANTS

(75) Inventors: Shihe Fan, Edmonton (CA); Steven Charles Grossnickle, North Saanich (CA); Marlies Rise, Victoria (CA); Stephen M. Attree, Victoria (CA); Raymund Folk, Sidney (CA)

(73) Assignee: Cellfor Inc., Saanichton, British Columbia (CA)

( * ) Notice: Subject to any disclaimer, the term of this patent is extended or adjusted under 35 U.S.C. 154(b) by 0 days.

(21) Appl. No.: 12/847,165

(22) Filed: Jul. 30, 2010

(65) Prior Publication Data
US 2010/0297771 A1  Nov. 25, 2010

Related U.S. Application Data

(62) Division of application No. 10/726,574, filed on Dec. 4, 2003, now Pat. No. 7,795,029.

(51) Int. Cl.
*C12N 5/00* (2006.01)
*C12N 5/02* (2006.01)

(52) U.S. Cl. .................. 435/240.54; 435/420; 435/430.1; 435/430; 435/240.4; 435/240.45

(58) Field of Classification Search ............. 435/240.54, 435/240.4, 240.45, 422, 430.1, 430, 420
See application file for complete search history.

(56) References Cited

U.S. PATENT DOCUMENTS
6,444,467 B1 * 9/2002 Fan et al. .................. 435/430.1

* cited by examiner

*Primary Examiner* — Annette H Para

(57) ABSTRACT

The invention provides a nutrient medium useful for sowing a somatic plant embryo or germinant of conifer species, which comprises particles of a solid component present within a flowable or semi-solid component containing water and a carbohydrate nutrient for the embryos or germinants. The nutrient medium has a fluidity such that at least some of the flowable or semi-solid component containing the carbohydrate nutrient remains in contact with the embryos or germinant at least until the embryo or germinant establishes vigorous growth under environmental conditions effective for such growth. The particles of the solid component are adapted to remain in contact with the embryo or germinant after of the flowable or semi-solid material dissipates, thereby providing continuing physical support for the embryo or germinant after the dissipation.

10 Claims, 2 Drawing Sheets

NUTRIENT MEDIUM USED FOR EX VITRO SOWING, GERMINATION, GROWTH AND CONVERSION OF PLANT SOMATIC EMBRYOS OR GERMINANTS

CROSS-REFERENCE TO RELATED APPLICATIONS

This application is a division of our prior patent application Ser. No. 10/726,574 filed Dec. 4, 2003. The entire contents of patent application Ser. No. 10/726,574 are specifically incorporated herein by this reference.

FIELD OF THE INVENTION

This invention relates to the sowing, germination, growth, and conversion of somatic embryos or germinants of conifer species. More particularly, the invention relates to sowing, and development of somatic embryos or germinants ex vitro in a porous solid growth substrate, such as soil or peat, to allow the embryos or germinants to develop into autotrophic seedlings and subsequently into mature plants in non-sterile conditions.

BACKGROUND OF THE INVENTION

Dependence on the use of zygotic seed in breeding programs, where success relies on seed availability, particularly that of genetically superior seeds, often leads to low returns on investment. The situation is exacerbated in tree breeding and improvement programs especially where conifer species are used, because the time span from flower bud initiation to seed maturation is usually one to three years. Climatic events and pest infection contribute to seed production variability from year to year (Harlow and Harrar 1968).

The development and advancement of somatic embryogenesis as a vegetative propagation technology has made it possible to mass-produce genetically identical individuals through the asexual reproduction of a source explant (Tautorus et al. 1991, Roberts et al. 1995). This technology allows for the application of clonal forestry in plantation programs. The primary advantages of clonal forestry as defined by Kleinschmit et al. (1993) and Park et. al. (1998a) are: 1) the ability to capture a greater portion of the non-additive genetic gain from selected individuals within a breeding population; 2) the capability to rapidly introduce individuals with desirable traits to meet known site conditions; and 3) the ability to carefully plan genetic diversity into plantation programs. The primary challenge in utilising somatic embryogenesis for clonal forestry in plantation programs is the development of cost effective and scaleable methods of somatic embryo culture to produce autotrophic and acclimatised seedlings.

Somatic embryogenesis of woody plants is generally a multi-step process (reviewed by Sutton and Polonenko, 1999; U.S. Pat. Nos. 4,957,866; 5,183,757; 5,294,549; 5,413,930; 5,464,769; 5,482,857; 5,506,136; the disclosure of all of which are herein incorporated by reference). No matter how diverse the different somatic embryogenesis protocols might be, the one common step is that somatic embryos must be germinated to produce somatic seedlings.

For zygotic embryos in natural seed, germination is supported by stored nutrients within the endosperm (in angiosperms) or megagametophyte (in gymnosperms). Major forms of storage nutrients in the nutritive tissues are starch, proteins and lipids which are broken down into simple substrates for us in various biochemical and physiological activities during germination. For somatic embryos, nutrients needed to support germination must be supplied by a nutrient medium during somatic embryo culture. There are two standard approaches for germinating somatic embryos. The first approach utilises conventional in vitro methods and is generally comprised of the following steps. First, a naked somatic embryo (i.e., an embryo unprotected by any coatings) is sown, using aseptic techniques, onto sterilised semi-solid or liquid media contained within a solid-support such as a Petri dish or a phytatray under sterile conditions. Second, after the somatic embryo has germinated and grown under sterile conditions, the young seedling is transplanted into conventional nursery growing systems. The second approach utilises encapsulation (generally gel-encapsulation) of the somatic embryos (Carlson and Hartle 1995, Gray et al., 1995; U.S. Pat. Nos. 4,562,663; 4,777,762; 4,957,866; 5,010,685; 5,183,757; 5,236,469; 5,427,593; 5,451,241; 5,486,218; 5,482,857 all of which are herein incorporated by reference) prior to germination. The embryos are encapsulated in various coating materials to form so-called "artificial seed", "synthetic seed" or "manufactured seed". This encapsulation process may or may not incorporate nutrients into the encapsulating medium, and provides a means by which the embryos can presumably be sown with conventional nursery seeding equipment (i.e., drum seeders or fluid drill seeders) into conventional nursery growing systems. The prior art makes references to sowing artificial seeds ex vitro into germination media comprised of soil or soil-less mixes, but in fact, the prior art only teaches methods for germinating artificial seeds in vitro, i.e., on sterilised semi-solid laboratory media. No approaches are taught or otherwise disclosed in the prior art for sowing encapsulated somatic embryos and/or artificial seed and/or manufactured seed into conventional growing systems using conventional sowing equipment.

The past dependence of somatic embryo germination on in vitro methods stems from the anatomical distinction between somatic embryos and zygotic seeds: a somatic embryo lacks the nutritive tissues and the protective seed coat that a zygotic seed possesses. Consequently, somatic embryos had to rely on exogenous nutrient supply for germination and early growth and these events had to take place in sterile environments in vitro for protection against both physical and biological damaging agents such as environmental stresses and microbial pathogens.

There are many disadvantages associated with in vitro protocols. The most significant are: 1) the repeated manual handling of each individual embryo in the germination and transplanting steps; 2) the stringent requirement for sterile techniques and culture conditions through all steps until somatic germinants are transplanted out of the in vitro germination environment into horticultural growing media; and 3) the difficulty in acclimatizing in vitro plantlets into ex vitro nursery environments. Therefore, the art of traditional in vitro protocols has an inherent nature of low efficiency and high cost, characteristics that are prohibitive to mass production of somatic seedlings. These undesirable characteristics make the commercial production of somatic seedlings less competitive than that of the zygotic seedlings (Sutton and Polonenko 1999). Automation, including robotics and machine vision, may reduce or eliminate the extensive manual-handling that is currently necessary to germinate naked somatic embryos. However, no commercial equipment currently exists which can reliably, aseptically, and cost-effectively perform the in vitro protocols for germination and gorwht of naked somatic embryos and subsequent transplanting of seedlings into conventional propagation systems (Roberts et al., 1995; reviews by Sakamoto et al., 1995; and Sutton and Polonenko 1999).

There are also numerous biological and operational disadvantages inherent in using gel-encapsulated somatic embryos. Biologically, the most significant disadvantage is the much lower germination vigour and conversion success into plants than corresponding zygotic seeds, as seen in the prior art protocols for encapsulating or otherwise coating somatic embryos (Redenbaugh et al., 1993; Carlson & Hartle, 1995; Gray et al., 1995). This is in sharp contrast with the germination vigour and conversion success of non-encapsulated or non-coated somatic embryos, produced with methods disclosed in the art, and then sown using aseptic techniques onto in vitro germination media in sterile conditions. The conversion rates of germinants from in vitro sown somatic embryos can approximate those of the corresponding zygotic seeds (e.g., greater than 85%) (Gupta and Grob, 1995).

Timmins et al. (U.S. Pat. No. 5,119,588, incorporated herein by reference) recognised that "somatic embryos are too under-developed to survive in a natural soil environment" and therefore must be "cultured with an energy source, such as sucrose". They identify a method by which plant somatic embryos can be sown into horticultural containers filled with particulate soil-like substrates. Solutions containing compounds serving as carbon and energy sources and other nutrients, such as minerals and vitamins, are added to the substrates before or after the embryos are sown. Because such a "culture medium is highly susceptible to invasion by phytopathogens, which can result in death or retard the growth of the embryos", they teach that the containers, substrate, nutrient solutions and other components of their system must be biologically sterile. Somatic embryos must be sown into containers using aseptic techniques. Each sown container must be kept biologically separated from the others and from the external environment and must be kept in a sterile condition until the embryo has successfully germinated and developed into a complete, independent autotrophic plant. Only after autotrophy has been reached can the somatic seedlings be removed from the sterile conditions and then transplanted into a conventional commercial propagation environment. Even though the art taught by such methods may be practised to produce somatic seedlings, such methods are labour-intensive and bear characteristics of low efficiency, high cost and impracticability for mass production of somatic seedlings in a nursery environment.

The inventors named herein have previously discovered that plant somatic embryos can be directly sown ex vitro in a variety of soil or soil-like growing media in non-sterile conditions (PCT patent application no. WO 09/965293A1, incorporated herein by reference), particularly plant somatic embryos that have been pre-germinated (U.S. Pat. No. 6,444,467 and U.S. patent application Ser. No. 09/550,110). In these patents and patent applications, exogenous energy and nutrient sources are still delivered to plant somatic embryos after they have been directly sown ex vitro in soil or soil-like growing media to facilitate and maximize the ex vitro growth of, somatic embryos.

Nevertheless, there is a constant need for improvement of these techniques and methods in order to overcome the disadvantages of the germination and growth phases associated with somatic plant embryos.

SUMMARY OF THE INVENTION

An object of the present invention is to provide a method enabling the production of complete, independent, autotrophic plants from conifer somatic embryos preferably in conventional nursery conditions (i.e. non-sterile, ex vitro conditions).

Another object of the present invention is to provide a "nutrient medium" to meet the requirements for successful development of conifer somatic embryos or pre-germinated conifer somatic embryos (germinants) in conventional nursery conditions.

According to one aspect of the present invention, there is provided a method of sowing a heterotrophic somatic plant embryo or germinant of a conifer species to facilitate growth into an autotrophic seedling, which method comprises the following steps: providing a nutrient medium comprising particles of a solid component contained within a flowable or semi-solid component containing water and a carbohydrate nutrient for the embryo or germinant; dispensing a quantity of the nutrient medium onto a surface of a porous solid growth substrate for the somatic plant embryo or germinant and contacting said plant embryo or germinant with the nutrient medium; and exposing the embryo or germinant to environmental conditions suitable for development into an autotrophic seedling; wherein at least the dispensing, contacting and exposing steps are carried out ex vitro in non-sterile conditions; and wherein the particles forming the solid component are adapted to remain in contact with the embryo or germinant after the flowable or semi-solid component undergoes dissipation, thereby providing continuing physical support for the embryo or germinant after such dissipation.

The nutrient medium of the present invention can take a variety of forms, including flowable or semi-solid media of various degrees of hardness with core and non-core ingredients. The core ingredients are usually water, simple organic and inorganic plant nutrients, and protective agents against phytopathogens. Non-core ingredients are usually gelling and structural filling agents. Together, the core and non-core ingredients form a water-containing flowable or semi-solid nutrient medium. The organic nutrients may comprise simple carbohydrates, such as sucrose, glucose, fructose, and maltose as carbon and energy sources, amino acids, plant growth regulators, vitamins, fatty acids and/or other compounds that are beneficial to the germination and growth of conifer somatic embryos. The inorganic nutrients may comprise both macro- and micro-elements that are essential to plant life. The protective agents include pesticides such as insecticides, fungicides, antibiotics, and/or other broad-spectrum biocides that protect conifer somatic embryos from insect and phytopathogens that can cause death or growth retardation to conifer somatic embryos or germinants. The gelling agents may comprise such substrates as, but are not restricted to, methylcellulose, agar, agarose, phytagel, Kelcogel® and gelcarin. These gelling agents can be added into the nutrient medium singularly or in combination. The gelling agents play a role in binding all components of the nutrient medium into a homogeneous, lasting, nutritional matrix to support the development of conifer somatic embryos or germinants. The solid component may comprise biologically inert water-insoluble substrates, such as, but not limited to, α-cellulose fiber, milled or sifted peat moss, perlite, vermiculite, clay, diatomaceous earth, coir or silica. The solid component acts as a structural filling agent which functions to anchor the conifer somatic embryo or germinant during growth while the gelling agent is dissolving away in the nutrient medium under the actions of soil microbes, heat, and cyclic soil wetting and drying. Preferably, the nutrient medium should contain a sufficient amount or proportion of the solid component to prevent toppling (loss of intended orientation) of at least the majority (and ideally substantially all) embryos or germinants until the embryos or germinants are autotrophic and anchored in the growth substrate by developed roots.

The nutrient medium may be formulated in either sterile or non-sterile conditions, preferably non-sterile for reasons of simplicity. When a gelling agent is not present in the nutrient medium, the nutrient medium does not need to be autoclaved, or heated. Autoclaving or heating is necessary only when there is gelling agent in the nutrient medium, as heat is needed to melt gelling agents to enable them to dissolve during medium preparation.

In accordance with another preferred aspect of the present invention, the nutrient medium is dispensed onto a porous solid growing substrate in growing containers, preferably conventional multi-cavity miniplug nursery containers. In addition, the growing substrate should be pre-wetted and may be charged with conventional fertilizers. The containers can be sterile or non-sterile, and are preferably non-sterile. The dispensing of the nutrient medium into the containers can be done by hand or by machinery, preferably by machinery. The amount of nutrient medium that is added into each individual container or each individual cavity of a multi-cavity miniplug container may vary depending upon the species of conifer somatic embryo and the container cavity size.

The conifer somatic embryos are preferably placed in direct contact with the nutrient medium by hand or by machinery, being sown onto or into the nutrient medium so that water and nutrients can be utilised for development of the embryo or germinant. The sowing process can be practised in sterile or non-sterile conditions, preferably non-sterile conditions.

The sown containers can be placed in sterile or non-sterile conditions, preferably conventional non-sterile nursery conditions, to allow the plant somatic embryos or germinants to grow into complete, independent, autotrophic plants. Conventional nursery conditions typically provide high relative humidity, warm air temperature, and sufficient light to meet the growth and development requirements of germinating or pre-germinated conifer somatic embryos. Consequently, the somatic seedlings produced from somatic embryos will have not required the transplanting or acclimation measures commonly associated with in vitro seedlings.

If desired, the somatic plant embryo may be pre-germinating prior to contacting the somatic plant embryo with the nutrient medium. The embryos are preferably sown with their root radicles pointing down and the remainder of the embryo in an upright position.

The flowable or semi-solid component is preferably a material having a structural integrity such that at least some of said flowable or semi-solid component containing the carbohydrate nutrient remains in contact with said embryo or germinant until said embryo or germinant is capable of autotrophic growth under the environmental conditions and a fluidity under said environmental conditions such that it may be dispensed under gravity or pressure from an orifice onto the porous solid growth substrate. The somatic plant embryo or germinant may be contacted with the nutrient medium after the nutrient medium has been dispensed onto the surface of the porous growth substrate, before the nutrient medium has been dispensed onto the surface of the porous growth substrate, or as said nutrient medium is dispensed onto said surface of the porous growth substrate. Most preferably, at least a part of the embryo or germinant remains exposed to the air after being sown in contact with the nutrient medium. This allows oxygen exchange with the embryo or germinant during its subsequent growth.

The porous solid growth substrate is preferably in the form of a body provided with a depression formed in the upper surface, and the nutrient medium is dispensed into the depression onto the surface. The embryo is then at least partially inserted into the depression in contact with the nutrient medium. The embryo is preferably sown naked.

The solid component of the nutrient medium may be of any solid, water-insoluble, biologically inert material or soil-like substrate such as α-cellulose fiber, milled or sifted peat moss, perlite, vermiculite, clay, diatomaceous earth, coir or silica. The solid components may include equi-axial particles or elongated particles, such as flexible fibers like those of α-cellullose and milled or sifted peat moss. The solid material is preferably present in the range up to 10% w/v, and more preferably between 3 and 8% (w/v), more preferably between 3 and 5% (w/v). The medium preferably also contains methylcellulose to prevent separation of the medium during storage. The concentration of the methylcellulose in the nutrient medium is between 0 and 6% w/v, more preferably 0.3 to 2% w/v. The nutrient medium is preferably a flowable or semi-solid medium containing the carbohydrate in dissolved form. If the nutrient medium contains a semi-solid component, it is preferably a flowable gel containing the carbohydrate in dissolved form. The gel may be formed by using a gelling agent, e.g. methylcellulose, agar, agarose, phytagel, gellan gum (e.g. Kelcogel®), and gelcarin. When the gelling agent is agar, it is preferably present in a concentration in the nutrient medium of less than 1.2% w/v, preferably 0.3 to 0.8% w/v. When the gelling agent is phytagel, it is preferably present in a concentration in the nutrient medium between 0 and 1.2% w/v, preferably 0.1 to 0.4% w/v. When the gelling agent is gelcarin, it is preferably present in a concentration in the nutrient medium between 0 and 1.2% w/v, more preferably 0.3 to 0.8% w/v.

The nutrient medium may additionally contain one or more mineral compounds, vitamins, amino acids, plant growth regulators and pest control compounds.

The carbohydrate nutrient present in the nutrient medium may be a monosaccharide, such as glucose or fructose, or an oligosaccharide, such as sucrose, maltose, raffinose or stachyose. The carbohydrate source in the nutrient medium may also be a combination of monosaccharides, a combination of oligosaccharides, or a combination of monosaccharides with oligosaccharides. Ideally, the carbohydrate nutrient is sucrose present in the nutrient medium in an amount in the range of in the range 1 to 10% (w/v), preferably 1 to 6% (w/v), and more preferably 1 to 4% (w/v). Alternatively, the carbohydrate nutrient may be maltose present in the nutrient solution in an amount in the range of in the range of 1 to 10% (w/v), preferably 1 to 6% (w/v), more preferably 1 to 4% (w/v).

The embryos or germinants may be of any conifer species, e.g. embryos are from the family Pinaceae, preferably of the pine (*Pinus*) genus including a variety of pine species and hybrids, e.g. *Pinus* hybrids selected from the group consisting of *Pinus rigida*×*Pinus taeda, Pinus taeda*×*Pinus rigida, Pinus serotina*×*Pinus taeda*, and *Pinus taeda*×*Pinus serotina*. Particularly suitable are embryos of loblolly pine (*Pinus taeda* L.), radiata pine (*Pinus radiata* D. Don.). Also suitable are embryos of the spruce (*Picea*) genus including a variety of spruce species and hybrids, as well as embryos of the species Douglas-fir (*Pseudotsuga menziesii* Mirb. Franco).

The somatic embryos are generally mature embryos in at least one of the following states:
  a) freshly matured embryos, having received no desiccation treatments after maturation and prior to being sown in direct contact with said nutrient medium;
  b) partially dried by a high relative humidity drying treatment after maturation and prior to being sown in direct contact with said nutrient medium;

c) desiccated by a severe drying treatment after maturation and prior to being sown in direct contact with said nutrient medium;

d) cold-stored at temperatures between 10 and 0° C. after maturation and prior to being sown in direct contact with said nutrient medium; and e) frozen-stored at temperatures between 0 and −190° C. after maturation and prior to being sown in direct contact with said nutrient medium.

The somatic embryos, before being sown in direct contact with the nutrient medium, may have received at least one of the following pre-treatments:

(a) in an original state without a pre-germination treatment;
(b) the embryos are pre-germinated.

The embryos are preferably sown in a multiple cavity miniplug tray using soil, or a soil-like material as the substrate. Examples of soil-like materials are peat and peat products, which may be used in combination with an extender such as vermiculite or perlite. However, non-peat based soil-like materials may also be used. The soil-like material may be bound together with a polymer.

The non-sterile growing conditions used for germinating and growing the embryos may include temperatures within the range of 10 and 35° C., more preferably 15 to 30° C., atmospheric relative humidity within the range of 20 and 100%, more preferably 60 to 100%, carbon dioxide concentration within the range of 0.003 and 3%, preferably between 0.003 and 0.03%; light level within the range of 0 and 2000 $\mu mol\ m^{-2}s^{-1}$ Photosynthetically Available Radiation (PAR), in a light/dark diurnal cycle within the range between 24 h/0 h and 0 h/24 h. The light/dark diurnal cycle is preferably between 16 h/8 h and 20 h/4 h, and the light level is preferably between 15 and 500 $\mu mol\ m^2 s^{-1}$ PAR. Ideally, the temperature, atmospheric relative humidity, carbon dioxide, light, and diurnal light/dark cycle conditions are created in non-sterile growing spaces such as conventional greenhouses, specifically constructed growth chambers, and/or specifically constructed growth rooms.

Additional nutrient medium may be supplied after sowing the embryos or germinants, e.g. a carbohydrate-containing and/or macro or micro nutrient-containing aqueous liquid applied by spraying, misting, drenching or irrigating. Spraying and misting are preferred in order to reduce the speed at which the original nutrient medium is dispersed.

According to another aspect of the invention, there is provided a method of growing an autotrophic seedling from a somatic plant embryo or germinant of a conifer species, which method comprises the following steps carried out ex vitro in non-sterile conditions: providing a nutrient medium comprising particles of a solid component present within an aqueous, flowable or semi-solid component containing a carbohydrate nutrient for the embryo or germinant; dispensing a quantity of the nutrient medium onto a surface of a porous solid growth substrate for the somatic plant embryo or germinant held in a container; contacting the plant embryo or germinant with the nutrient medium; and subjecting the embryo to environmental conditions to cause development of the embryo or germinant into an autotrophic conifer seedling; wherein the nutrient medium has a cohesiveness such that at least some of the flowable or semi-solid component containing the carbohydrate nutrient remains in contact with the embryo or germinant as the embryo or germinant proceeds to full germination and/or conversion to autotrophy under appropriate environmental conditions; and wherein the particles of the solid component are adapted to remain in contact with the embryo or germinant after of the flowable or semi-solid material dissipates, thereby providing continuing physical support for the embryo or germinant after such dissipation.

The present invention also relates to the nutrient medium used in the method above, and to seedlings produced by the method.

In preferred forms of the invention, the method of sowing or growing somatic embryos or germinants begins with the preparation of conifer somatic embryos prior to germination. This can be achieved by methods already known in the art.

The entire process of nutrient medium preparation, nutrient medium application, embryo or germinant sowing, germination, and growth can be (and preferably is) practised in non-sterile conditions. Each of these steps can be automated if so desired.

Consequently, aseptic techniques, equipment, and conditions are no longer necessary for successful development of conifer somatic embryos or germinants to produce autotrophic seedlings.

There are several advantages associated with the present invention, at least in its preferred forms. One advantage is that the nutrient medium provides a continuous supply of water and nutrients to the conifer somatic embryo or germinant at least for early ex vitro growth and development until the flowable or semi-solid component dissipates. Water in the nutrient medium also buffers the conifer somatic embryo or germinant from water stress in open ex vitro conditions, which could arise from low air humidity or low soil water content.

Another advantage, at least of preferred forms of the invention, is that the nutrient medium contains a solid component that provides continuing physical support to the embryos or germinants as the other components drain away or disappear, thus allowing the embryos or germinants to remain in a proper upright position until a root develops to anchors it into the porous solid growth substrate.

Another advantage of this invention, at least in its preferred forms, is that the nutrient medium, by virtue of its flowable or semi-solid properties, provides a homogenous matrix for close contact between the conifer somatic embryo or germinant and the matrix. This facilitates the absorption of nutrients and water by the conifer somatic embryos or germinants and eliminates poor plant-soil contact that is often associated with ex vitro seedlings on non-semi-solid or non-flowable, particulate-like growing media.

In its preferred forms, another advantage of this invention is that the conifer somatic embryos or germinants may be sown directly into soil (or other solid growth substrate) in nursery containers and remain there for subsequent growth stages. Consequently, there is no need for costly transplanting and acclimation of somatic seedlings, which are disadvantageous features of in vitro seedlings.

An additional advantage of this invention, at least in preferred forms, is that the ex vitro conifer somatic embryos or germinants do not require aseptic techniques, equipment or conditions for development. The sowing and transplanting into large containers, when needed, can be done using automated nursery equipment. This allows for low-cost mass production of high quality somatic seedlings.

If desired, the nutrient medium may be added into a solid growth substrate in containers. Solid growth substrates include, but are not limited to, soil or soil-like substrates, natural or artificial. Consequently, conifer somatic embryos or germinants will grow directly into soil without the need of multi-step hand or machine-handling. The soil or soil-like substrates can be sterile or non-sterile, but are preferably non-sterile.

The solid growth substrate may be provided in conventional nursery containers. Such containers can vary in size, but are preferably multi-cavity miniplug containers. The containers can be sterile or non-sterile, but are preferably non-sterile.

The conifer somatic embryos or germinants may be sown directly onto or into the nutrient medium in the solid growing support in the containers. Such a sowing process can be performed either by hand or by machinery, but preferably by machinery.

The entire process may be operated in non-sterile conditions, from the steps of nutrient medium formulation, nutrient medium application, embryo or germinant sowing, and development of the conifer somatic embryos or germinants into complete, independent, autotrophic plants in soil. Consequently, no aseptic techniques, equipment, conditions, and no acclimation steps as commonly required by in vitro germinants are needed. Seedlings so produced may be grown in the original container or may be transplanted at a later date into large or commercial sized containers.

The non-sterile conditions may be those found in a conventional nursery environment. Therefore, the entire process can be practised in accordance with the operation of a nursery.

The present invention includes the above objects and features taken alone or in combination. These and other features, objects, and advantages of the present invention will become readily apparent to those skilled in the art upon reading the following detailed description.

DEFINITIONS

Figure 1:
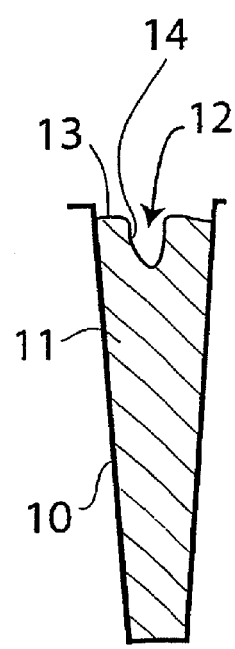
FIGS. 1 to 5 schematically show examples of steps involved in the sowing, development and growth of somatic embryos in according to a preferred method according to the present invention.

A number of terms are known to vary in meaning in the literature describing this art. The following definitions are believed to be those most commonly used in the fields of botany and plant somatic embryogenesis, and are consistent with the usage of the terms in the present specification, including the claims. These definitions will assist in the understanding of the detailed description of the present invention that will follow.

"Acclimatise" or "acclimatize" refers to the adaptation to a new temperature, climate, or environmental condition, etc. For embryos germinated in vitro on semi-solid media, acclimatisation refers to the processes involved in the seedlings successfully adapting to ex vitro environments in the greenhouse or nursery, and subsequently resuming vigorous growth and development.

"Ampicillin" is an antibiotic.

"Autotrophic" refers to the stage of plant development in which the photosynthetic organelles, related enzymes and biochemical pathways are completely functional and capable of converting light energy, atmospheric carbon dioxide and water into the prerequisite carbohydrates (e.g., glucose) necessary to sustain further plant growth and development. Autotrophic plants are able to survive and grow under normal soil conditions.

"BA" is benzyl adenine, a cytokinin-type of plant growth regulator. The main physiological effect of BA is to stimulate cell division.

"Benlate" is a registered trademark for benomyl (methyl 1-(butylcarbamoyl)-2-benzimidazolecarbamate), which is a fungicide.

"Clone", when used in the context of plant propagation, refers to a collection of individuals having the same genetic constitution and is produced from an individual plant or a culture that arises from an individual explant.

"Conversion" refers to the transition from a heterotrophic stage of plant development to an autotrophic stage of plant development. The term "converted" as applied to an embryo or germinant means an embryo or germinant that has undergone conversion and is autotrophic.

"Desiccation" refers to the drying of a somatic embryo by any means to a water content less than that of the original hydrated embryo. Desiccation processes may include (a) mild desiccation, which encompasses water contents in the 36-55% water content range, and (b) severe desiccation, which occurs at water contents less than 36%, usually in the range of 5-30%. A fully desiccated viable embryo is able to survive freezing, and after rehydration, is able to successfully complete the germination process and convert to a normal, autotrophic plant.

"Endosperm" is strictly an angiosperm seed structure, and is always triploid due to double fertilisation. The endosperm contains the nutritive reserves required for zygotic embryo development and growth when the germination process is started.

"Explant" is the organ, tissue or cells derived from a plant and cultured in vitro for the purposes of starting a plant cell or tissue culture.

"Flowable" means that a material flows under its own weight or can be caused to flow under light force or pressure (i.e. forces or pressure of the kind encountered in sowing operations).

"Frozen storage" refers to storage of embryos at less than the freezing point of water, and preferably at a temperature in the range of −10° C. to −190° C. "GA" is an abbreviation for gibberellins, a group of related growth regulator isomers (e.g., $GA_3$, $GA_4$, and $GA_7$) that are naturally synthesized as a normal part of plant metabolism. The main physiological effect of GA is to stimulate elongation of individual plant cells. Exogenous applications of GA can be used to stimulate, manipulate and accelerate the initiation and growth of shoots and roots.

"Gelcarins" are purified carrageenans, which are a naturally occurring family of polysaccharides derived from red seaweed.

"Genotype" refers to the genetic constitution of an organism, acquired from its parents and available for transmission to its offspring. When used in the context of asexual plant propagation, genotype is interchangeable for clone.

"Germinant" refers to a somatic embryo that has been pre-germinated but not converted.

"Gnatrol®" is a biological larvicide. The active ingredient of this product is Bacillus thuringiensis subspecies israelensis.

"Heterotrophic" refers to the stage of plant development when the photosynthetic organelles, related enzymes and biochemical pathways are still not completely functional or capable of converting light energy, atmospheric carbon dioxide and water into the prerequisite carbohydrates (e.g., glucose) necessary to sustain further plant growth and development. Consequently, heterotrophic plants still require an exogenous supply of carbon and energy resources in the growth medium such as sucrose, to sustain normal growth and development until the plants become completely autotrophic.

By definition, heterotrophic plants are not able to survive and grow under normal soil conditions.

"HRHT" stands for a high relative humidity drying treatment, which is a partial drying process for somatic embryos performed in a high relative humidity range of 85-99.9%. The treatment is carried out by the method of the Roberts patent (U.S. Pat. No. 5,183,757, incorporated herein by reference).

"IAA" is indole-3-acetic acid, an auxin-type plant growth regulator naturally synthesised as a normal part of plant metabolism. The main physiological effect of IAA is to stimulate meristematic cell division, cell enlargement and differentiation. Exogenous applications of IAA can be used to stimulate, manipulate and accelerate the initiation and growth of shoots and roots.

"IBA" is indole-3-butyric acid, a synthesised analogue of IAA. IBA can be used to affect the initiation of roots and shoots in the same manner as exogenous applications of IAA.

"Megagametophyte" refers to haploid nutritive tissues of gymnosperm seed, maternal in origin within which the gymnosperm zygotic embryos develop.

"Nutrients" are the inorganic micro- and macro-minerals, vitamins, hormones, organic supplements, and carbohydrates necessary for culture growth and somatic embryo development.

"Nutrient solution" refers to water containing a dissolved nutrient or mixture of nutrients.

"Penicillin" is an antibiotic.

"Pre-germination" refers to a process of contacting a mature somatic embryo with medium for any period of time until onset of autotrophic development.

"Root radicle" refers to the meristematic end of a germinating embryo from which roots develop. This is an area in which undifferentiated cell division is rapid, with the resulting cells then undergoing a period of elongation behind the root radicle before transformation into differentiated cells.

"Seed" refers to the ripened ovule consisting of the zygotic embryo, its proper nutritive tissues and coat.

"Seedling" refers to a conifer somatic plant that is autotrophic and/or has a well-developed epicotyl.

"Semi-solid" used in connection with a component of a nutrient medium refers to a consistency of the component of the nutrient medium such that it does not flow under its own weight, but can be made to flow by applying light pressure or force.

"Somatic embryo" refers to a plant embryo formed in vitro from vegetative (somatic) cells by mitotic division of cells. Early stage somatic embryos are morphologically similar to immature zygotic embryos, and comprise a region of embryonic cells subtended by elongated suspensor cells.

"Somatic embryogenesis" is the process of initiation and development of embryos in vitro from somatic cells and tissues.

"Water potential" is defined as the free energy per unit volume of water, assuming the potential of pure water to be zero under standard conditions. Water potential of a cell or plant is the sum of osmotic, turgor, and matric potential. Osmotic potential is the component produced by solutes dissolved in the cell sap. Turgor potential is produced by diffusion of water into protoplasts enclosed in cell walls that resist expansion. Matric potential refers to water held by colloids, on surfaces and in microcapillaries in the cells and cell walls. Both the osmotic and matrix potential reduce the free energy of water whereas turgor potential increases the free energy of water. Water potential in a cell or plant is usually negative. Water potential and its components are customarily expressed in pressure units, such as Pascal (Pa) or mega-Pascal (MPa).

"Water stress" refers to situations in which plant water potential and turgor potential are reduced enough to interfere with normal functioning under dehydration (drought) conditions. Water stress can also be caused by excessive water in the rooting zone.

"Zygotic embryo" is an embryo derived from the sexual fusion of gametic cells.

DETAILED DESCRIPTION OF THE INVENTION

The present invention relates to a method of sowing a somatic plant embryo or germinant, nutrient media for use in the method, and a method for producing complete, independent, autotrophic seedlings utilizing the method of sowing. In particular, the invention is concerned with somatic embryos or germinants from conifer species and methods carried out in non-sterile ex vitro conditions, preferably using essentially naked embryos or germinants. This enables the invention, at least in its preferred forms, to be carried out relatively inexpensively, on a large (even mass-produced) scale of operation, using equipment and facilities that are common in the plant-growing concerns.

The invention makes use of a carbohydrate- and water-containing nutrient medium that is provided in contact with the somatic embryos or germinant as they are sown on or in a solid porous growth substrate. The nutrient medium provides for delivery of water and nutrients (including one or more carbohydrates) to conifer somatic embryos or germinant for growth, and also preferably provides physical support for the embryo to keep it oriented in the correct (upright) position until sufficient root growth for anchoring the plant has taken place. The nutrient medium contains a component consisting of solid particles and a component that is flowable or semi-solid. The fluidity (viscosity) of the medium is preferably such that the flowable or semi-solid component is not immediately absorbed into a porous solid growth substrate on which the medium is dispensed during sowing. In fact, the fluidity is such that the medium, and the carbohydrate it contains, remains in contact with the embryo during its period of germination. The medium can also provide immediate physical support for the embryo. When the flowable or semi-solid component is eventually fully absorbed by the growth material or otherwise removed from the surroundings of the embryo, the solid component (solid particles) remains to provide continued physical support for the embryo so that it can continue to develop roots and to mature without disruption caused by a lack of physical support. The method, including the manufacturing and application of the nutrient medium, can be practised in conventional non-sterile conditions using conventional horticultural practices, equipment, and facilities.

In a particularly preferred form, the following steps may be carried out:

1. The conifer somatic embryos are pre-germinated. The pre-germination treatment may or may not include initial culture on a semi-solid medium to be followed by liquid culture. Initial culture on a semi-solid medium may not be essential particularly if: (a) fresh, mature conifer somatic embryos are to be used; and (b) conifer somatic embryos are not to be pre-germinated. After the completion of the pre-germination treatment, the vigour and synchrony of the pre-germinated conifer somatic embryos are generally substantially increased as compared to those conifer somatic embryos that are not pre-germinated. The art of the pre-germination treatment is detailed in U.S. Pat. No. 6,444,467 and U.S. patent application Ser. No. 09/555,110 (incorporated herein by reference).

The liquid culture step of the pre-germination methods starts with the transfer of plant somatic embryos into a vessel containing a liquid medium. The liquid medium contains at least one source of carbohydrates, such as, but is not restricted to, sucrose in the range of 1-6% (w/v). The liquid medium also contains other types of nutrients that may further facilitate the various biochemical and physiological processes occurring during development. Such nutrients include, but are not restricted to, inorganic mineral elements, amino acids, vitamins, and plant hormones.

The conifer somatic embryos are preferably cultured in liquid medium for a period of time in the range of one to five days and preferably between three to four days. Throughout the liquid culture, the embryos are suspended within the solution and are kept in constant motion. A non-limiting example of how this might be accomplished is by securing the vessels containing the embryos and liquid medium onto a shaker table which is revolving at a rate in the range of 40-120 rpm, preferably in the range of 80-100 rpm. Since it is known in the art that zygotic seeds of certain plant species will germinate in the dark while zygotic seeds of other plant species require light for successful germination, pre-germination may be practised in either the presence or absence of light.

It is preferable throughout pre-germination that aseptic techniques be used. It is therefore preferable that the pre-germination vessels and the media used during pre-germination are sterilised prior to the addition of the conifer somatic embryos, and that an aseptic technique is used when adding embryos to media. It is also preferable that the contents of the pre-germination vessels be maintained in a sterile condition during the pre-germination process. However, it should be noted that is not essential to pre-germinate conifer somatic embryos in order to practise this invention.

2. The conifer somatic embryos (either pre-germinated or not pre-germinated) are sown by hand or by machinery, preferably by machinery, into nursery containers containing a porous solid horticultural growing substrate (actually, such substrates normally contain three phases all present simultaneously, i.e. solid particles, moisture and air—but would normally be referred to as solid substrates) and a flowable or semi-solid nutrient medium. The nutrient medium contains at least one source of carbohydrate that is a nutrient for the embryo. Although the preferred carbohydrate is sucrose, preferably present in the medium in an amount in the range of 1-6% (w/v), this invention can be practised with other carbohydrates such as fructose, glucose, maltose, galactose, mannose, lactose, etc. Furthermore, the nutrient medium may contain, if so desired, a mixture of two or more carbohydrates. If mixtures of carbohydrates are used in the nutrient medium, then the appropriate concentrations of each carbohydrate should be experimentally determined in advance by the use of rate-selection studies known to those skilled in this art.

In addition to carbohydrates, the nutrient medium may also contain, if so desired, other types of nutrients that may further facilitate various biochemical and physiological processes occurring during developmental phases from germination to conversion. Such nutrients include, but are not restricted to, inorganic mineral elements, organic acids, vitamins and plant hormones. The following is a non-limiting example of this practise. The nutrient medium may contain sucrose in the range of 1-6% (w/v), and a mixture of mineral nutrients formulated to deliver: 350 mg nitrogen/l, 186 mg phosphorus/l, 469 mg potassium/l, 25 mg calcium/l, 19.5 mg magnesium/l, 364 mg sulphur/l, 171 mg chlorine/l, 3 mg manganese/l, 0.5 mg zinc/l, 3 mg iron/l, 0.01 mg iodine/l, 0.6 mg boron/l, 0.01 mg molybdenum/l, 0.01 mg cobalt/l, and 0.01 mg copper/l, 1.2 mg L-glutamine/l, 0.1 mg L-alanine/l, 0.04 mg L-cysteine-HCl/l, 1.2 mg L-arginine/l, 0.02 mg L-leucine/l, 4.0 mg glycine/l, 4.0 mg L-serine/l, 1.0 mg L-asparagine/l, and 1.0 mg L-proline/l. Furthermore, if so desired, IBA, a plant growth regulator, may be added alone at a concentration of 0.05~0.1 µmol/l or in combination with one or both of GA and BA, each at a concentration of 0.05~0.1 µmol/l.

Furthermore, if so desired, pest control products such as antibiotics or fungicides may be added to the nutrient medium. A non-limiting example is the addition of Benlate (0.1 g/l) and/or Ampicillin (0.1 g/l).

Furthermore, if so desired, gelling agents may be added to the nutrient medium either singly or in combination. The gelling agent binds all components of the nutrient medium to form a flowable or semi-solid, nutritious matrix for development of plant somatic embryos or germinants. A non-limiting example is the addition of phytagel (0.2-0.3% w/v), agar (0.3-0.4% w/v), gelcarin (0.3-0.4% w/v) or methyl-cellulose (0.4-1.0% w/v).

Furthermore, a particulate solid component is incorporated into the nutrient medium, e.g. a filling agent such as α-cellulose, milled or sifted peat moss, perlite, vermiculite, clay, diatomaceous earth, coir or silica. The structural filling agent (solid component) supports the conifer somatic embryo germinant as the flowable or semi-solid dissolves away under the action of various forces such as soil microbes, heat, wetting and drying. A non-limiting example is α-cellulose or milled peatmoss in the range of 3-6% w/v. The particulate solid may be in the form or regular or irregular generally equi-axial particles or clumps, or may be in the form of elongated fibers, with elongated fibers being most preferred. The solid should be such that it remains around or against the embryo after the remainder of the nutrient medium has dispersed and provides a matrix or body that supports the embryo against toppling over or displacement.

It has also been found preferable to incorporate methylcellulose into the nutrient medium. This helps to prevent separation of the medium into solid and liquid phases, and it prevents clumping of the medium, and also helps to retain the medium on the solid porous substrate without rapid uptake by the substrate. It has been found that the addition of about 0.75%-1.0% by wt. methylcellulose in combination with 4-5% w/v α-cellulose or milled or sifted peat moss improves the consistency of the medium.

The nutrient medium is prepared prior to being added onto a porous solid horticultural growing substrate. It is not necessary to autoclave or heat the nutrient medium unless a gelling agent is included. If heating is required, the nutrient medium solution should be autoclaved or heated for a period of time in the range of 2 to 25 minutes, preferably 3 to 20 minutes, most preferably 3 to 10 minutes. Autoclaving or heating may be done using various forms of equipment, such as, but not restricted to, an autoclave, hot plate, stove, oven, or microwave oven. The autoclaved or heated nutrient medium can be added to the three-phase conventional growing substrate while it is still hot, but preferably it is cooled to room temperature. When a gelling agent is included at a low percentage concentration, such as phytagel at 0.2% w/v, agar at 0.3% w/v, or gelcarin at 0.3% w/v, the nutrient medium is a soft semi-solid after cooling. It can be agitated into a viscous but flowable medium. When such gelling agents are included at a lower percentage concentration than indicated above, the nutrient medium is viscous but flowable after cooling. In its preferred form, the nutrient medium should be kept fluid for dispensing onto the growing substrate.

Various devices with precision volume control mechanisms may be used to dispense the nutrient medium onto the growing substrate. A non-limiting example is a repeat pipette, a multi-channel pipette, or a precision pneumatic dispensing pump. In preferred forms of the invention, the growing substrate is pre-wetted with water and/or charged with fertilizer at 50 ppm nitrogen (such as 11-41-8, nitrogen-phosphorous-potassium) as well as with micro-nutrients. Generally, the nutrient medium is dispensed first onto the surface of the solid substrate, or in a depression formed in the surface, to form a pool, and then an embryo or germinant is placed at least partially in the pool of nutrient medium, ensuring that the embryo is oriented correctly for subsequent germination and growth. However, it would be possible to sow the embryo or germinant first, and then to dispense the nutrient medium to surround the embryo, at least partially. It is further contemplated that the embryo and nutrient medium may be dispensed at the same time, i.e. the embryo would be suspended in the nutrient medium, and the embryo would be dispensed within a droplet or pool of the nutrient medium onto the surface of the solid substrate or into a depression formed in the surface.

It is apparent from the above description that this entire step can be non-sterile. Consequently, commencing from this step, aseptic technique and sterile conditions are not required to successfully practise this invention.

3. Nursery containers sown with conifer somatic embryos or germinants are placed in conventional plant propagation environments (such as chambers, growth rooms or conventional greenhouses) in which light, temperature, atmospheric humidity, carbon dioxide, and water content of the rooting substrate can be controlled. This controlled nursery environment facilitates the further development of conifer somatic embryos or germinants into seedlings. The following conditions provide a non-limiting plant propagation environment for conifer species such as white spruce, loblolly pine, radiata pine, and Douglas-fir: light at 20-300 $\mu$mol $m^{-2}s^{-1}$ Photosynthetically Available Radiation (PAR), 18 hour day/6 hour dark photoperiod, 20-26° C. day and night air temperatures, 80-100% relative humidity for the first week with a gradually decrease in humidity to 50-70% over a three week period, and 0.015% carbon dioxide concentration. The ambient light intensity and diurnal photoperiod, temperature, atmospheric humidity and other such factors may be adjusted as required for each specific species during somatic embryo or germinant growth and their subsequent development and conversion into completely functional seedlings.

4. During the growing period, if so desired, an aerosol in the form of a mist or spray may be supplied to the surface of the nursery containers sown with somatic embryos or germinants. The aerosol may contain the necessary carbohydrate and other nutrient. Alternatively, the supplemental nutrients may be applied to the horticultural growing substrate in liquid form, directly adjacent to the plant somatic embryos, with a device having a precision volume control mechanism such as a pipette. However, it is not essential that carbohydrates, amino acids, vitamins, and plant hormones be supplemented during the ex vitro development processes. It is, however, necessary to continue the supplementation of macro- and micro-mineral elements during growth and development of the conifer somatic embryos or germinants to ensure successful autotrophic development. These macro- and micro-mineral elements may be supplemented through incorporation of commercial fertilisers in the normal greenhouse growing practices.

5. Conifer seedlings so produced may continue to grow to commercial size in the original containers under normal greenhouse growing regimes if the container sizes are sufficiently large to meet the growth requirements. Alternatively, seedlings grown in "miniplug" containers may be transplanted at a later date into large-sized containers to continue their growth and development under normal greenhouse conditions. Or, seedlings grown in miniplug containers may be transplanted at a later date into bare-root nursery beds if so required.

A feature of the present invention, at least in its preferred forms, is that the water and nutrient requirements of conifer somatic embryos or germinants for early growth and development are met through the presence of a nutrient medium prior to the plants becoming completely autotrophic. The addition of a nutrient medium allows the conifer somatic embryos or germinants to grow in a normal nursery environment. Because, at least in its preferred forms, the nutrients are contained in a gelled nutrient medium, the nutrients are long lasting. Also, because frequent irrigation of the pre-wetted and/or fertilized growing substrate is not required (though infrequent light misting can be beneficial), nutrients in the nutrient medium are not subjected to leakage from the growing substrate. Consequently, all nutrients originally incorporated in the nutrient medium and intended for the embryos or germinants can be utilised by the embryos or germinants for growth. Further to this, because conifer somatic embryos or germinants are directly sown on or in the nutrient medium, the nutrients in the nutrient medium are readily available. The advantage of this feature is that the presence of the nutrient medium reduces or eliminates the need for repeated application of exogenous nutrients after the conifer somatic embryos are sown, as described in PCT patent application no. WO 09/965293 A1, and U.S. Pat. No. 6,444,467 (incorporated herein by reference).

Another feature of the present invention, at least in its preferred forms, is that the formulation of the nutrient medium can vary according to the requirements of somatic embryos or germinants of different plant species. The requirements of different species may be experimentally determined in advance by studies. The design and performance of such studies are known to those skilled in the art. Furthermore, the nutrient medium may contain essential nutrients, but may also contain other components that are deemed beneficial for development of plant somatic embryos or germinants.

Another feature of the present invention, at least in its preferred form, is that although there exists a nutrient medium in the growing substrate, it does not exclude, if so desired, the addition of extra exogenous nutrients. These exogenous nutrients can include, but are not restricted to, carbohydrates and minerals applied by either aerosols or by injection or drenching. The nutrient solutions can be applied with, but are not restricted to, conventional misting and/or fogging equipment. The nutrients can be applied individually or combined into one solution. A non-limiting example of this practise is the application of a nutrient solution containing 3% sucrose (w/v), 350 mg nitrogen/l, 186 mg phosphorus/l, 469 mg potassium/l, 25 mg calcium/l, 19.5 mg magnesium/l, 364 mg sulphur/l, 171 mg chlorine/l, 3 mg manganese/l, 0.5 mg zinc/l, 3 mg iron/l, 0.01 mg iodine/l, 0.6 mg boron/l, 0.01 mg molybdenum/l, 0.01 mg cobalt/l, and 0.01 mg copper/l. If so desired, the plant growth regulator IBA may be added alone at a concentration of 0.1 µmol/l or in combination with GA and BA, separately or together, each at a concentration of 0.05~0.1 µmol/l. Another non-limiting example is to separately apply sucrose and mineral elements. The mineral nutrients can be supplied as a commercial formulation such as but not restricted to 10-52-10 (nitrogen-phosphate-potassium) or 11-41-8 (nitrogen-phosphate-potassium). Another alternative non-limiting means of supplying exogenous nutrients to somatic embryos or germinants sown onto growing substrate within nursery containers is to irrigate or "drench" the growing substrate with nutrient solutions formulated as previously described by using any conventional or specially designed multiple mini-injectors. Alternatively, the exogenous nutrients may be delivered to each individual embryo or germinant with a device having a precision volume control mechanism, such as but not restricted to, a repeater pipette, a multi-channel pipette or pneumatic pump.

Another feature of the present invention, at least in its preferred forms, is that special hygienic and/or aseptic and/or sterile handling methods and/or equipment and/or facilities are not required to successfully handle, sow and grow desiccated or hydrated fresh embryos or pre-germinated conifer somatic embryos. All steps, excluding pregermination, may be carried out in non-sterile, non-hygienic and/or non-aseptic conditions, i.e., those types of conditions typically encountered in conventional horticultural or forest nursery plant propagation environments.

Still another feature of the present invention, at least in its preferred forms, is that the sowing and propagation of conifer somatic embryos or germinants can be practised with a wide variety of non-sterilised growing substrates in a wide variety of non-sterilised growing containers commonly used in conventional plant propagation. The preferred growing substrate is peat-based and has been formulated specifically for germination of zygotic seed. Examples of such mixtures are (a) 100% short-fibre peat product polymerised with a water-binding polymer, (b) 15.2 cu. ft of peat, 8 cu. ft. of vermiculite, 680 grams of dolomite lime, and 300 grams of Micromax®, and (c) 16.2 cu. ft. of peat, 6.75 cu. ft. perlite, 4 cu. ft. vermiculite, 6 kilograms of dolomite lime, 1.5 kilograms of gypsum, 375 grams of potassium phosphate, 250 grams Micromax®, and 35 grams of wetting agent. Alternatively, commercially formulated mixes can also be used with the present invention. It is preferred that the peat-based growing substrate be moistened to a water content in the range of 59-75% and then dispensed into growing containers. It should be noted that the present invention could be practised in substrates other than peat-based mixtures. Such substrates could be, but are not restricted to, the following materials: peat plugs, composted or shredded coconut husk fibres commonly referred to as "cor" or "coir", extruded foams, and rock wool. Regardless of the rooting substrate chosen, its physical characteristics should enable development and maintenance of a high relative humidity in the gaseous phase, i.e., in excess of 75% RH within the substrate, while minimising saturation of the substrate with the liquid phase.

The preferred growing containers are multi-cavity nursery containers, commonly referred to as miniplug trays, flats, or cell-packs. Such containers are commonly used to produce plant plugs that can be mechanically transplanted into larger containers for continued growth under greenhouse conditions or into bare-root seedling beds in a field-growing environment. The present invention can be practised by using any multi-cavity trays, or alternatively, with individual pots. A non-limiting example are miniplug trays filled with 100% short-fibre peat product polymerised with a water-binding polymer.

Nursery containers sown with conifer somatic embryos or germinants are preferentially placed in a conventional plant propagation environment. The desired plant propagation environment consists of, but is not limited to, the ranges of temperatures of 15-35° C., relative humidities of 50-100%, photosynthetic photon flux of 15-500 µmol $m^{-2}$ $s^{-1}$ PAR, diurnal cycles of 6 h day/18 h night to 22 h day/2 h night, and a carbon dioxide concentration of 0.003-0.02%. Although other conditions may vary, it is preferable that atmospheric relative humidity around the containers sown with conifer somatic embryos is maintained in the range of 80-100% for at least the first three to seven days. There are many methods that may be used to achieve these levels of relative humidity. A non-limiting example is to place the containers in a greenhouse environment with misting or fogging equipment that is deployed at controlled intervals. Another non-limiting example is to place the containers in a fogging or misting tent, chamber or room such as, but not restricted to, a horticulture chamber or room. After the germinants are established as evidenced by the growth or furthered development of cotyledons, epicotyl and root structures, the atmospheric relative humidity may be gradually reduced and the germinants integrated into conventional nursery cultural practices.

Micro-organisms such as insects, fungi, bacteria, yeast, and algae are ubiquitous in conventional plant propagation substrates, equipment, containers and growing environments. Because the present invention is practised in non-sterilised conditions, this presence in the environment may reach a pathogenic level at various stages of plant development. It is therefore prudent that normal nursery pest management and hygiene measures are practised to reduce the probabilities of an outbreak. When pests do occur, a wide variety of chemicals and biological pesticide products are available to control and eradicate plant pathogens. Pesticides such as Gnatrol®, Benlate®, Rovril®, Trumpet®, which are registered for pest control in plant crops, can be used in conjunction with somatic embryos or germinants. A non-limiting prevention example is to incorporate Benlate (0.1 g/l) and Ampicillin (0.1 g/l) in the nutrient medium so that the immediate rooting zone environment is kept free of fungi and bacteria for as long as the pesticides are still in effect. Another non-limiting example is to use 5-10 ml Gnatrol®/l to eradicate fungus gnat larvae.

As already noted above, the solid component contained in the nutrient medium provides continuing physical support for the embryo or germinant, even after the liquid or semi-solid components have dispersed. If a solid component of this kind is not provided, the embryo or germinant may begin to develop a rudimentary root, but the root may be insufficient to anchor it in the growing substrate before the surrounding nutrient medium disperses. The embryo or germinant may consequently lose its desired orientation with respect to the surface of the growing substrate and may consequently face in the wrong direction or loose contact between the root and the growing substrate. In either case, conversion to healthy plants will be compromised. In contrast, the solid component becomes packed around the embryo or germinant and keeps it in the correct orientation. Any amount of solid in the nutrient medium will help with this objective, but clearly more is better than less provided there is not so much that the fluidity of the medium and its nutrient and water contents are compromised. Suitable ranges of amounts can be determined experimentally, but the indications provided above are effective.

The support of the embryo or germinant can be further enhanced by providing a depression for the embryo or germinant and nutrient medium in the surface of the growing substrate. This is illustrated in FIGS. 1 to 5 of the accompanying drawings. FIG. 1 shows a nursery container 10, preferably a mini-plug tray (the container 10 forming one well of the miniplug tray) filled almost to the top with a porous solid growth substrate 11, e.g. soil, peat or a soil-like product bound together with a polymer. A slight depression 12 is made in the upper surface 13 of the substrate, the inside of the depression has a substrate surface 14.

Figure 2:
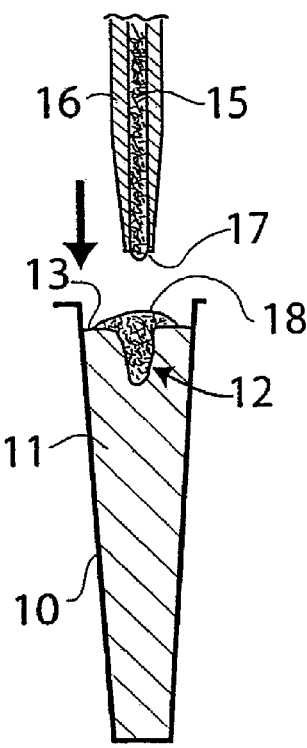

As shown in FIG. 2, a flowable or semi-solid nutrient medium 15 is dispensed onto the substrate 11 in the container 10 from a hollow tubular device 16 having a lowermost orifice 17. The medium has a fluidity such that it can be dispensed in this way by gravity or by pressure (e.g. elevated air pressure). The medium 15 enters the depression 12 and contacts the inner substrate surface 14 and forms a pool or body 18 on the upper surface 13.

Figure 3:
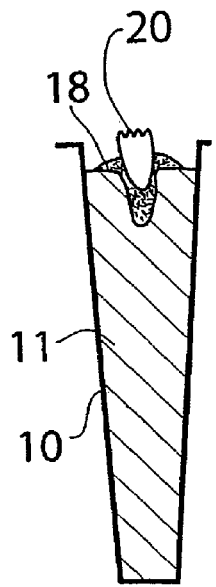

As shown in FIG. 3, a somatic embryo (or germinant) 20 is then sown in the container 10. This is achieved by a holding device (e.g. a tube connected to a vacuum pump—not shown in the drawing) which brings the embryo (or germinant) 20 into contact with the pool or body 18 of nutrient medium 15. The embryo (or germinant) does not have to be submerged in the nutrient medium and may be only partially submerged as shown in FIG. 3 with at least part of the embryo exposed to air. However, the medium provides support for the embryo (or germinant) so that it remains in the desired upright orientation.

Figure 4:
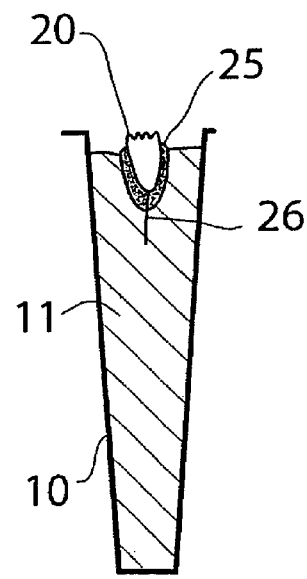
Figure 5:
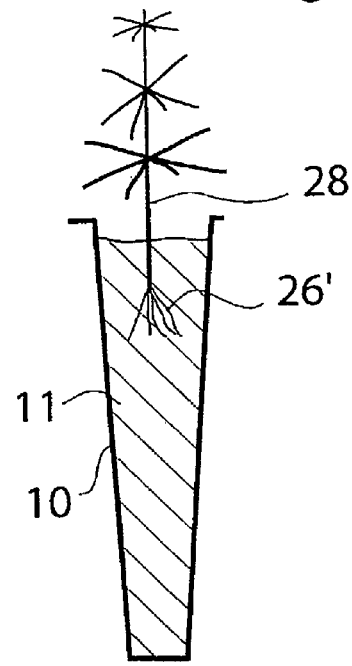

The pool or body 18 of nutrient medium 15 has sufficient cohesiveness to remain in place in contact with the embryo (or germinant) at least until germination of the embryo is complete, thus assuring the embryo (or germinant) a source of water and carbohydrate nutrient. Eventually, though, the flowable or semi-solid component of the nutrient medium disperses, e.g. by being absorbed into the growth substrate 11 or by being broken down by microorganisms. When this takes place, the solid component 25 of the nutrient medium remains in place around the embryo (or germinant) 20 as shown in FIG. 4. This provides the embryo (or germinant) with physical support to prevent it toppling over or otherwise being dislodged while the emergent root 26 is still in a juvenile condition. This keeps the embryo (or germinant) facing in the correct upright direction until the root becomes established, as shown at 26', and the seedling 28 becomes developed (FIG. 5). The solid component of the nutrient medium may become an indistinguishable part of the growth substrate as the seedling develops.

The following Examples are provided to further illustrate the present invention and are not to be construed as limiting the invention in any manner.

EXAMPLE 1

The objective of this experiment was to study the effects of different carbohydrate compositions in nutrient medium used for ex vitro growth of conifer germinants from somatic embryos.

Methods

Traditionally, sucrose is the primary carbon and energy source in plant tissue culture media. Mature plant somatic embryos are routinely germinated in vitro on sucrose nutrient medium and grown into transplantable plants. Maltose and other soluble carbohydrates may be used in various stages of somatic embryogenesis, such as in maintenance media for tissue proliferation and in maturation media for somatic embryo induction (see U.S. Pat. Nos. 4,801,545, 5,036,007 and 5,563,061). In in vitro studies carried out by the inventors of the present invention have shown that a variety of carbon sources, including a combination of glucose and fructose as well as sucrose, can promote growth of loblolly pine somatic embryos. Since sucrose hydrolyses into glucose and fructose in the medium (Tremblay and Tremblay, 1995), it is hypothesized that mixtures of simple carbohydrates, as compared to monotype carbohydrate, may similarly promote or improve growth of conifer somatic germinants.

Somatic embryos of Interior spruce (genotype IS 1) were desiccated and frozen-stored for 8 months. Somatic embryos of loblolly pine (genotype LP 1) and radiata pine (genotype RP 1) were stored in high relative humidity treatment (HRHT) plates at 4° C. for 9 months (according to Roberts U.S. Pat. No. 5,183,757). Somatic embryos of Douglas-fir (genotype DF 1) were desiccated and stored at 4° C. for 4 months. In this experiment, somatic embryos of interior spruce were first cultured on a 0.8% w/v phytagel semi-solid medium at room temperatures for two days. The cultured embryos, together with loblolly pine and radiata pine embryos, were then transferred to liquid medium (according to Fan and Janic U.S. patent application Ser. No. 09/550,110) for four days under similar conditions to complete pre-germination. This involved placing 80 embryos (for spruce, embryos cultured first on semi-solid medium) from each species in 50 ml of medium with 3% w/v sucrose, ½ m24GMD nutrient solution, 0.1 µM IBA, 0.6 mg/l L-glutamine, 0.05 mg/l L-alanine, 0.02 mg/l L-cysteine-HCl, 0.6 mg/l L-arginine, 0.01 mg/l L-leucine, 2.0 mg/l glycine, 2.0 mg/l serine, 0.5 mg/l L-proline, and 100,000 units/l penicillin, in a 250 ml Kimax® baffled Erlenmeyer culture flask. The flasks were place on a gyratory shaker (60 rpm) at ambient temperatures (20-23° C.) under a day/night diurnal cycle of 18/6 hours at 20-30 µmol m$^{-2}$s$^{-1}$ PAR provided by two 20-W cool white fluorescent lights. Douglas-fir embryos were first cultured on the same semi-solid medium at 12° C. for one week before being transferred to liquid medium for one day as described above. The liquid medium for Douglas-fir embryos also contained 0.1 g/l Ampicillin and 0.1 g/l Benlate.

Germinants were sown ex vitro in miniplug trays. Each cell in the miniplug trays was filled with 0.3 ml of nutrient medium in the center of the polymer-bound peat growing-medium. The nutrient medium consisted of the following basic ingredients: 0.2% w/v phytagel, 4% w/v α-cellulose, ½ m24GMD, 0.1 µM IBA, 0.1 µM BA, 0.1 g/l Benlate, and 0.1 g/l Ampicillin. Carbohydrate compositions and concentrations in the nutrient medium were as described in Table 1.1. Note that the medium volume was adjusted to accommodate the fact that 1 g of alpha cellulose occupied 1 ml of medium. In order to avoid variation in osmotic potential in the nutrient medium, the total molar concentration of carbohydrates in each treatment was fixed at the same level (i.e. 116.9 mM). Each treatment had 4 replicates of 21 germinants per genotype. The root radicles of the pre-germinated embryos were inserted by hand into the nutrient medium. After sowing, the miniplug trays were placed in a horticultural germination chamber with conditions, and fertility and pesticide regime similar to those described in Example 2. The survival percentage and morphological development results of the germinants were determined after three weeks of growth under non-sterile ex vitro conditions.

Results

The three-week ex vitro results are summarized in Table 1.1. No significant differences in %-survival and germinant growth were found among the treatments of nutrient medium with different carbohydrate sources tested.

Sucrose is the traditional carbohydrate used in tissue culture media. This example illustrated that the growth of somatic germinants from different conifer species can similarly benefit from different types or different combinations of carbohydrates in the nutrient medium. A variety of carbohydrate compositions can be used in nutrient medium to enhance germinant performance for each of the commercially important conifer species tested.

ent medium and assessed their effects on ex vitro growth of germinants from conifer somatic embryos.

Before experimental use, somatic embryos of interior spruce (genotype IS 1) were desiccated and frozen-stored for seven months. Somatic embryos of radiata pine (genotype RP 2) were stored in HRHT plates @4° C. for ten and nine months, respectively. In the experiment, somatic embryos of interior spruce were first cultured on a 0.8% w/v phytagel semi-solid medium at room temperatures for one day. These embryos, as well as radiata pine embryos, were then cultured in liquid medium for four days as described in Example 1.

Germinants were sown ex vitro in miniplug trays. Each cell in the miniplug trays contained 0.3 ml of nutrient medium. The nutrient medium consisted of the following basic ingre-

TABLE 1.1

Sucrose, glucose, fructose, and maltose concentrations in the various nutrient media and three-week survival percentage, and morphological development of conifer somatic embryos under ex vitro non-sterile conditions

| SPECIES | Genotype | Carbohydrate composition (g/l) | | | | Survival (%) | Shoot length (mm) | Root length (mm) |
| --- | --- | --- | --- | --- | --- | --- | --- | --- |
| | | Sucr. | Gluc. | Fruct. | Malt. | | | |
| INTERIOR SPRUCE | IS 1 | 40 | 0 | 0 | 0 | 97.6 ± 1.4 | 16.6 ± 0.5 | 15.3 ± 1.6 |
| | | 20 | 0 | 0 | 21.05 | 91.7 ± 4.1 | 16.9 ± 0.6 | 19.1 ± 1.8 |
| | | 13.33 | 7.02 | 7.02 | 0 | 88.1 ± 7.1 | 16.4 ± 0.5 | 18.5 ± 2.0 |
| | | 13.95 | 12.24 | 1.80 | 0 | 86.9 ± 2.3 | 16.2 ± 0.6 | 17.7 ± 1.9 |
| | | 9.19 | 8.11 | 8.11 | 0 | 83.3 ± 7.9 | 19.7 ± 2.6 | 19.8 ± 1.8 |
| | | 9.19 | 6.31 | 6.31 | 7.21 | 88.1 ± 7.5 | 16.7 ± 0.6 | 16.7 ± 1.9 |
| | | 0 | 7.21 | 3.60 | 20.49 | 89.3 ± 4.5 | 15.3 ± 0.5 | 16.2 ± 1.8 |
| | | 0 | 10.53 | 10.53 | 0 | 91.7 ± 4.1 | 17.8 ± 0.6 | 19.5 ± 1.7 |
| | | 0 | 0 | 0 | 42.10 | 96.4 ± 1.2 | 14.4 ± 0.4 | 12.5 ± 1.5 |
| LOBLOLLY PINE | LP 1 | 40 | 0 | 0 | 0 | 94.0 ± 3.0 | 8.1 ± 0.3 | 3.1 ± 0.7 |
| | | 20 | 0 | 0 | 21.05 | 94.0 ± 3.0 | 8.0 ± 0.3 | 2.9 ± 0.6 |
| | | 13.33 | 7.02 | 7.02 | 0 | 86.9 ± 2.3 | 8.5 ± 0.3 | 1.8 ± 0.3 |
| | | 13.95 | 12.24 | 1.80 | 0 | 71.4 ± 11.5 | 8.2 ± 0.4 | 3.0 ± 0.8 |
| | | 9.19 | 8.11 | 8.11 | 0 | 85.7 ± 4.8 | 7.6 ± 0.3 | 1.8 ± 0.4 |
| | | 9.19 | 6.31 | 6.31 | 7.21 | 81.0 ± 4.3 | 8.1 ± 0.4 | 2.7 ± 0.5 |
| | | 0 | 7.21 | 3.60 | 20.49 | 81.0 ± 5.1 | 8.1 ± 0.3 | 3.1 ± 0.5 |
| | | 0 | 10.53 | 10.53 | 0 | 91.7 ± 3.0 | 9.0 ± 0.3 | 3.8 ± 0.7 |
| | | 0 | 0 | 0 | 42.10 | 82.1 ± 7.9 | 7.4 ± 0.3 | 2.5 ± 0.6 |
| RADIATA PINE | RP 1 | 40 | 0 | 0 | 0 | 63.1 ± 11.1 | 7.5 ± 0.3 | 1.5 ± 0.5 |
| | | 20 | 0 | 0 | 21.05 | 64.3 ± 7.4 | 7.5 ± 0.3 | 3.0 ± 0.6 |
| | | 13.33 | 7.02 | 7.02 | 0 | 66.7 ± 4.3 | 7.7 ± 0.3 | 2.4 ± 0.6 |
| | | 13.95 | 12.24 | 1.80 | 0 | 53.6 ± 10.5 | 7.3 ± 0.3 | 2.0 ± 0.4 |
| | | 9.19 | 8.11 | 8.11 | 0 | 73.8 ± 8.1 | 7.3 ± 0.3 | 2.4 ± 0.5 |
| | | 9.19 | 6.31 | 6.31 | 7.21 | 54.8 ± 14.1 | 7.3 ± 0.3 | 2.6 ± 0.6 |
| | | 0 | 7.21 | 3.60 | 20.49 | 58.3 ± 6.6 | 7.0 ± 0.3 | 1.9 ± 0.4 |
| | | 0 | 10.53 | 10.53 | 0 | 82.1 ± 6.3 | 7.9 ± 0.3 | 1.7 ± 0.2 |
| | | 0 | 0 | 0 | 42.10 | 70.2 ± 6.3 | 6.7 ± 0.3 | 2.1 ± 0.6 |
| DOUGLAS-FIR | DF 1 | 40 | 0 | 0 | 0 | 86.9 ± 2.3 | 12.1 ± 0.4 | 4.1 ± 0.5 |
| | | 20 | 0 | 0 | 21.05 | 89.3 ± 3.0 | 11.4 ± 0.4 | 5.0 ± 0.6 |
| | | 13.33 | 7.02 | 7.02 | 0 | 76.2 ± 10.1 | 12.4 ± 0.4 | 4.6 ± 0.5 |
| | | 13.95 | 12.24 | 1.80 | 0 | 64.3 ± 8.8 | 11.9 ± 0.4 | 4.8 ± 0.4 |
| | | 9.19 | 8.11 | 8.11 | 0 | 77.4 ± 7.9 | 11.2 ± 0.3 | 5.0 ± 0.9 |
| | | 9.19 | 6.31 | 6.31 | 7.21 | 79.8 ± 4.9 | 13.1 ± 0.5 | 5.8 ± 0.7 |
| | | 0 | 7.21 | 3.60 | 20.49 | 67.9 ± 9.0 | 11.5 ± 0.3 | 5.3 ± 0.5 |
| | | 0 | 10.53 | 10.53 | 0 | 69.0 ± 12.1 | 12.6 ± 0.5 | 6.2 ± 0.5 |
| | | 0 | 0 | 0 | 42.10 | 86.9 ± 6.0 | 11.3 ± 0.3 | 6.7 ± 0.7 |

EXAMPLE 2

The objective of this study was to compare the effect of different gelling agents in nutrient medium on non-sterile ex vitro growth of conifer germinants from somatic embryos.

Methods

Many gelling agents are currently being used in the production of tissue culture media. Agar is by far the most popular although phytagel is gaining recognition. Gelcarin is a cheaper alternative to agar and phytagel. This experiment compared the use of agar, phytagel, and gelcarin in the nutridients: 4% w/v α-cellulose, 4% w/v sucrose, ½ m24GMD, 0.6 mg/l L-glutamine, 0.05 mg/l L-alanine, 0.02 mg/l L-cysteine-HCl, 0.6 mg/l L-arginine, 0.01 mg/l L-leucine, 2.0 mg/l glycine, 2.0 mg/l serine, 1.0 mg/l proline, 0.1 g/l Benlate, 0.1g/l Ampicillin, 0.1 μM IBA and 0.1 μM BA. The gelling agents and their concentrations in the nutrient medium were described in Table 2.1. Note that the medium volume was adjusted to accommodate the fact that 1 g of alpha cellulose occupied 1 ml of medium. After sowing was completed, the trays were placed in a horticultural growth chamber. Environmental conditions in the chamber were as follows: 20-90 $\mu$mol m$^{-2}$s$^{-1}$ PAR provided by eight 40-W fluorescent lights, 22-25° C. air temperature, and 60-100% RH. During the experimental period, 0.1 g/l Benlate, 0.1 g/l Ampicillin solutions were used to control fungi and bacteria when needed. On the first day of the third week, all treatments were fertilized with 0.5 g/l 20-20-20 all-purpose fertilizer. The %-survival and morphological development of germinants were determined after three weeks of growth under non-sterile ex vitro conditions.

Results

This example demonstrated that variation in the type and strength of the gel in the nutrient medium had no significant effect on the survival and morphological development of the germinants after three weeks of non-sterile ex vitro growth (Table 2.1). Though gel strength and type had no effect on germinant growth, the inclusion of a gelling agent in the medium reduces the separation of liquid and solid phases of the medium. This helps to keep dissolved nutrients in a more confined region of the miniplug, where the germinant is establishing early growth. The presence of a gelling agent in the medium also improves the structural integrity of the medium. Although this has no effect on germinant growth, it is important to help improve germinant stability in miniplugs. This is important to help prevent germinants from being washed out of miniplugs during watering and fertilization prior to extensive root development. It is especially important for germinant culture in a nursery (as opposed to chamber) environment (see Example 10). In addition, gelling agents in nutrient medium may also help to keep dissolved nutrients near the germinants for a longer period of time than if the nutrients were dissolved in a fluid that could run down into the subtending miniplug cells.

months), radiata pine (genotype RP 3, stored in HRHT plates at 4° C. for six months) and Douglas-fir (genotypes DF 2 and 3, desiccated and stored @4° C. for two months). Embryos of interior spruce and radiata pine were pre-germinated for four days following the same protocol as described in Example 1. Douglas-fir embryos were cultured on a semi-solid medium for two weeks @12° C. before receiving a one-day liquid culture treatment (also as described in Example 1).

Germinants were sown ex vitro in miniplug trays as described in Example 1. To each cell in the miniplug trays, 0.3 ml of nutrient medium was added. The nutrient medium consisted of the following ingredients: 0.2% w/v phytagel, 4% w/v sucrose, ½ m24GMD, 0.1 µM IBA, 0.6 mg/l L-glutamine, 0.05 mg/l L-alanine, 0.02 mg/l L-cysteine-HCl, 0.6 mg/l L-arginine, 0.01 mg/l L-leucine, 2.0 mg/l glycine, 2.0 mg/l serine, 0.1 g/l Benlate, and 0.1 g/l Ampicillin. The α-cellulose fiber was tested at 0, 3, 5, 7, and 10% w/v levels. Each of these treatments had four replicates of 21 germinants sown for each Genotype. Note that the medium volume was adjusted to accommodate the fact that 1 g of alpha cellulose occupied 1 ml of medium.

The root radicles of germinants were inserted by hand into the nutrient medium. After sowing, the miniplug trays were placed in a horticultural germination chamber with conditions, and fertility and pesticide regimes similar to those described in Example 2. On the first day of the second week, a 0.3 ml liquid medium similar to the nutrient medium (with phytagel and α-cellulose absent) was added into each cell in each nutrient medium treatment. The %-survival and morphological development of the germinants were determined after three weeks.

TABLE 2.1

%-survival and morphological development of conifer germinants from somatic embryos after three weeks of growth under non-sterile ex vitro conditions

| SPECIES | Genotype | Agar (% w/v) | Phytagel (% w/v) | Gelcarin (% w/v) | Survival (%) | Shoot length (mm) | Root length (mm) |
|---|---|---|---|---|---|---|---|
| INTERIOR SPRUCE | IS 1 | 0 | 0 | 0 | 86.8 ± 11.5 | 13.8 ± 0.6 | 4.4 ± 0.6 |
| | | 0.3 | | | 95.0 ± 3.5 | 13.2 ± 0.5 | 4.3 ± 0.5 |
| | | 0.4 | | | 91.3 ± 2.4 | 11.0 ± 0.5 | 4.7 ± 0.4 |
| | | 0.5 | | | 96.3 ± 2.4 | 12.4 ± 0.4 | 3.8 ± 0.5 |
| | | | 0.1 | | 92.5 ± 3.2 | 13.6 ± 0.5 | 3.3 ± 0.5 |
| | | | 0.2 | | 90.0 ± 5.0 | 11.6 ± 0.3 | 3.1 ± 0.3 |
| | | | 0.3 | | 95.2 ± 3.4 | 11.8 ± 0.5 | 3.6 ± 0.6 |
| | | | | 0.3 | 96.3 ± 1.3 | 13.6 ± 0.6 | 5.2 ± 0.7 |
| | | | | 0.4 | 88.8 ± 6.6 | 12.4 ± 0.5 | 5.8 ± 0.7 |
| | | | | 0.5 | 81.3 ± 9.7 | 11.8 ± 0.4 | 4.2 ± 0.3 |
| RADIATA PINE | RP 2 | 0 | 0 | 0 | 48.0 ± 6.3 | 8.0 ± 0.5 | 2.8 ± 0.4 |
| | | 0.3 | | | 68.8 ± 9.2 | 11.1 ± 1.5 | 2.6 ± 0.3 |
| | | 0.4 | | | 63.8 ± 8.3 | 8.6 ± 0.5 | 3.5 ± 0.3 |
| | | 0.5 | | | 81.3 ± 8.3 | 9.2 ± 0.4 | 1.4 ± 0.3 |
| | | | 0.1 | | 66.3 ± 9.0 | 11.2 ± 0.5 | 2.0 ± 0.5 |
| | | | 0.2 | | 77.5 ± 12.7 | 9.4 ± 0.5 | 1.8 ± 0.2 |
| | | | 0.3 | | 76.5 ± 5.1 | 10.2 ± 0.5 | 2.1 ± 0.3 |
| | | | | 0.3 | 68.8 ± 6.3 | 10.2 ± 0.4 | 1.8 ± 0.3 |
| | | | | 0.4 | 60.0 ± 10.8 | 9.5 ± 0.4 | 2.2 ± 0.3 |
| | | | | 0.5 | 75.0 ± 5.4 | 10.5 ± 0.6 | 3.4 ± 0.7 |

EXAMPLE 3

The objective of this study was to examine various concentrations of α-cellulose in nutrient medium used for non-sterile ex vitro growth of germinants from conifer somatic embryos.

Methods

Experimental embryos were taken from interior spruce (genotype IS 2), stored on HRHT plates at 4° C. for six The reason for inclusion of α-cellulose into the nutrient medium is that gelled nutrient medium sinks into miniplugs over a two-week period, which renders young germinants sown in miniplug cavities unstable. In this experiment, the inclusion of α-cellulose into the nutrient medium was intended to anchor the germinants and prevent toppling. The α-cellulose had no intended nutritional benefit; however, this material was intended to provide structural support in the miniplug cavity. Thus, a neutral or positive effect on germinant performance was seen as a beneficial result for inclusion of α-cellulose into nutrient medium.

Results

For all species and genotypes tested, ex vitro %-survival was similar for all nutrient medium treatments (Table 3.1). In addition, there were no significant differences in shoot and root growth for all genotypes of Douglas-fir, interior spruce and radiata pine tested in the control nutrient medium treatment (0% α-cellulose) and the nutrient medium treatments containing α-cellulose.

The addition of α-cellulose in nutrient medium had neither a positive nor a negative effect on survival of germinants from conifer somatic embryos. However, the addition of α-cellulose to nutrient medium provided structural support to germinants and prevented toppling in the miniplug cavities. An α-cellulose level <3% w/v did not provide sufficient support to germinants. Too much α-cellulose in nutrient medium (>7% w/v) reduced the fluidity of the medium, making it difficult to apply the nutrient medium to miniplug trays. The use of α-cellulose between 3% w/v and 7% w/v α-cellulose concentrations consistently produced a dispensable medium that provided sufficient structural support to germinants, and did not sink into miniplugs during the three weeks miniplugs were maintained in the horticultural growth chamber.

of 10 μmol $m^{-2}s^{-1}$ PAR. The pre-germination solution contained 3% w/v sucrose, m24GMD or re-modified m24GMD, 0.1 μM IBA, and amino acids (as in Example 1).

Somatic embryos of Douglas-fir (genotypes 2a and 2b) were produced in bioreactors. Mature embryos were bulk-sorted and desiccated. The desiccated embryos were stored at 4° C. for 3 months. Embryos were cultured on semi-solid medium in petri plates for 18 days at 12° C. These embryos with normal morphology (i.e. with symmetrical cotyledons, a hypocotyl, and root meristem) were hand-selected from the population and transferred to liquid culture for three days in 250 ml Kimax® baffled culture flasks. The flasks contained liquid medium made with m24GMD and 3% w/v sucrose, 0.1 μM IBA, and amino acids (as in Example 1). The flasks were placed on a gyratory shaker (100 rpm) under laboratory conditions of 19-22° C. ambient temperature and a one 1 hour photoperiod of 10 μmol $m^{-2} s^{-1}$ PAR provided by one 20-W fluorescent light.

Germinants were sown ex vitro in miniplug trays containing nutrient medium. The nutrient medium contained 0.2% w/v phytagel, 2% w/v sucrose, 2% w/v maltose, 4.5% w/v cellulose, m24GMD or re-modified m24GMD, amino acids, 0.1μM IBA, 0.1 μM BA, 0.1 g/l Ampicillin, and 0.1 g/l Benlate. Note that the medium volume was adjusted to accommodate the fact that 1 g of alpha cellulose occupied 1 ml of

TABLE 3.1

%-Survival and morphological development of Douglas-fir, interior spruce, and radiata pine somatic embryos under non-sterile ex vitro conditions in response to GEM without α-cellulose and with α-cellulose at four concentrations.

| Species | Genotype | α-Cellulose (% w/v) | Survival (%) | Shoot length (mm) | Root length (mm) |
|---|---|---|---|---|---|
| Douglas-fir | DF 2 | 0 | 78.6 ± 5.7 | 13.5 ± 0.4 | 10.0 ± 0.5 |
| | | 3 | 69.0 ± 10.4 | 12.4 ± 0.4 | 8.6 ± 0.5 |
| | | 5 | 83.3 ± 4.1 | 13.8 ± 0.4 | 8.8 ± 0.4 |
| | | 7 | 72.6 ± 13.0 | 13.9 ± 0.5 | 10.0 ± 0.6 |
| | | 10 | 83.3 ± 4.1 | 13.6 ± 0.4 | 9.7 ± 0.6 |
| | DF 3 | 0 | 90.5 ± 3.9 | 10.5 ± 0.3 | 5.1 ± 0.3 |
| | | 3 | 86.9 ± 4.9 | 10.2 ± 0.4 | 4.4 ± 0.3 |
| | | 5 | 94.0 ± 3.6 | 11.6 ± 0.4 | 4.9 ± 0.4 |
| | | 7 | 95.2 ± 3.4 | 10.9 ± 0.4 | 5.2 ± 0.3 |
| | | 10 | 96.4 ± 3.6 | 11.0 ± 0.3 | 5.4 ± 0.4 |
| Interior Spruce | IS 2 | 0 | 81.0 ± 5.1 | 12.9 ± 0.4 | 6.4 ± 0.5 |
| | | 3 | 92.9 ± 4.1 | 12.5 ± 0.4 | 7.1 ± 0.5 |
| | | 5 | 85.7 ± 2.7 | 12.5 ± 0.4 | 6.8 ± 0.7 |
| | | 7 | 95.2 ± 3.4 | 12.4 ± 0.4 | 6.4 ± 0.6 |
| | | 10 | 83.3 ± 3.1 | 11.9 ± 0.4 | 6.9 ± 0.6 |
| Radiata Pine | RP 3 | 0 | 94.0 ± 2.3 | 4.0 ± 0.2 | 2.4 ± 0.1 |
| | | 3 | 95.2 ± 3.4 | 3.8 ± 0.2 | 2.1 ± 0.1 |
| | | 5 | 96.4 ± 2.3 | 4.3 ± 0.2 | 2.5 ± 0.3 |
| | | 7 | 91.7 ± 2.3 | 4.1 ± 0.2 | 2.2 ± 0.1 |
| | | 10 | 90.5 ± 3.9 | 3.7 ± 0.2 | 2.1 ± 0.1 |

EXAMPLE 4

The objective of this study was to assess the ex vitro conversion of interior spruce and Douglas-fir germinants into fully functional commercial-grade seedlings.

Methods

Somatic embryos of interior spruce (genotypes. IS 3, 4 and 5) were stored in HRHT plates for 13 months at 4° C. Embryos were pre-germinated for four days in a liquid medium in vented Lifeguard© polycarbonate boxes on a gyratory shaker (85 rpm) in a growth chamber. The following conditions were maintained in the growth chamber: 20/22° C. (cycling 16 and 8 hrs respectively) with a one 1 h photoperiod medium. For interior spruce, 8 replicates of 20 germinants were sown for each genotype and liquid medium treatment (i.e. m24GMD and rm24GMD). For Douglas-fir, one replicate of 77 (genotype 2a) and one replicate of 83 (genotype 2b) germinants were sown.

Douglas-fir germinants were grown for three weeks, and interior spruce germinants were grown for seven weeks in a horticultural growth chamber (under similar environmental conditions, and fertility and pesticide regimes as described in Example 2). Germinants were then transferred to a greenhouse environment. Douglas-fir was maintained for 13 weeks in the greenhouse (for a total of 16 weeks growth ex vitro), and Interior spruce was maintained for five weeks in the greenhouse (for a total of 12 weeks ex vitro). Three environmental zones were required for growing germinants into young somatic seedlings in a greenhouse environment. These three zones provided conditions that allowed for the transition of germinants from the chamber environment to the greenhouse environment (i.e., from low light levels & high humidity to decreasing humidity and higher light levels). Listed below are the greenhouse environmental conditions that the germinants were transitioned through during seedling growth.

1) Temperature: from 22 to 16° C.
2) Lighting: from 100 to 1200 µmol m$^{-2}$s$^{-1}$ PAR
3) Humidity: from 85-92% RH to 50-70% relative humidity
4) Fertilization/irrigation: from 11-41-8 NPK at 50 ppm N to 19-9-18 NPK at 100 ppm N
5) Pest control—same as Example 2 throughout culture period At the end of the ex vitro growth periods, %-survival, % conversion and heights were measured for interior spruce and Douglas-fir seedlings. In addition, merchantability was assessed for Douglas-fir seedlings.

Results

The %-survival, %-conversion and heights of seedlings for three genotypes of interior spruce are shown in Table 4.1, and for Douglas-fir, data are shown in Table 4.2. This example confirmed that conifer somatic embryos can be germinated and then sown ex vitro in miniplugs with nutrient medium to produce merchantable miniplug seedlings (see also Example 8).

TABLE 4.1

%-Survival, %-conversion, and height of interior spruce somatic seedlings after twelve weeks of ex vitro development.

| Genotype | Medium | Survival (%) | Conversion (%) | Height (mm) |
|---|---|---|---|---|
| IS 3 | m24GMD | 63.1 ± 4.6 | 58.8 ± 4.2 | 28.4 ± 1.1 |
| | Re-m24GMD | 69.4 ± 4.8 | 58.8 ± 3.0 | 30.2 ± 3.4 |
| IS 4 | m24GMD | 87.6 ± 1.9 | 84.8 ± 2.1 | 29.2 ± 0.7 |
| | Re-m24GMD | 85.7 ± 3.8 | 76.8 ± 3.3 | 29.7 ± 0.9 |
| IS 5 | m24GMD | 23.1 ± 5.7 | 21.9 ± 5.3 | 14.0 ± 0.9 |
| | Re-m24GMD | 20.0 ± 2.1 | 18.1 ± 2.5 | 16.3 ± 1.1 |

Re-m24GMD denotes re-modified m24GMD medium treatments.

TABLE 4.2

%-Survival, %-conversion, height, and merchantability of miniplug seedlings produced from Douglas-fir germinants after 16 weeks of ex vitro development.

| Genotype | Replicate | Total Germinants Sown | Survival (%) | Total Conversion (%) | Seedling Grade | % of Sown Germinants | Seedling Height (mm) |
|---|---|---|---|---|---|---|---|
| DF 2b | 1 | 83 | 86.8 | 78.3 | Merchant-able | 71.1 | 37.8 ± 1.3 |
| | | | | | Rejected | 7.2 | 11.2 ± 1.2 |
| DF 2a | 2 | 77 | 87.0 | 68.8 | Merchant-able | 54.5 | 41.9 ± 1.5 |
| | | | | | Rejected | 14.3 | 10.2 ± 1.1 |

EXAMPLE 5

The objective of this example was to determine a proper combination of methyl-cellulose and α-cellulose in nutrient medium in order to improve the consistency of the medium as it relates to storage (especially to eliminate gel separation and clumping with medium storage) and retention in the miniplug cavities.

Methods

Nutrient medium was prepared containing the following ingredients: rm8GMD macro nutrients, micro nutrients and vitamins, amino acids (Table 5.1), 3% w/v sucrose, 0.1 µM IBA, 0.05 µM BA, Benlate (0.1 g/l), Ampicillin (0.1 g/l), alpha cellulose, methylcellulose and phytagel.

TABLE 5.1

Amino Acids in Nutrient Medium.

| Amino acid | mg/l |
|---|---|
| L-Glutamine (mg/l) | 73.00 |
| L-Glutamic acid (mg/l) | 36.75 |
| L-Alanine (mg/l) | 4.45 |
| L-Arginine (mg/l) | 69.60 |
| L-Leucine (mg/l) | 6.55 |
| Glycine (mg/l) | 7.50 |
| L-Serine (mg/l) | 10.50 |
| L-Asparagine (mg/l) | 33.00 |
| L-Proline (mg/l) | 23.0 |
| L-Histidine | 7.76 |
| L-Tryptophan | 10.21 |

The phytagel, α-cellulose and methylcellulose were assessed at the levels described in Table 5.2. Note that the medium volume was adjusted to accommodate the fact that 1 g of alpha cellulose occupied 1 ml of medium. Each of the nutrient medium combinations was placed in a refrigerator for one week to assess their stability (i.e., ability to stay as a mixture or to have separation of the liquid and solid components). In addition, separate batches of these treatments were applied at 0.4 ml to 5 replicates of 20 miniplug cells, for each treatment, to assess their structural stability in the miniplug cells.

TABLE 5.2

Treatments modifying nutrient medium consistency with varying concentrations of methylcellulose, phytagel and α-cellulose.
Treatments 1. 4.5% w/v α-cellulose, no methyl cellulose, 0.2% w/v phytagel (SOP)
2. 4.5% w/v α-cellulose, 1% w/v methyl cellulose, 0.1% w/v phytagel
3. 5% w/v α-cellulose, 1% w/v methyl cellulose, 0.1% w/v phytagel TABLE 5.2-continued Treatments modifying nutrient medium consistency with varying concentrations of methylcellulose, phytagel and α-cellulose.
Treatments 4. 4.5% w/v α-cellulose, 1% w/v methyl cellulose, 0.2% w/v phytagel
5. 5% w/v α-cellulose, 1% w/v methyl cellulose, 0.2% w/v phytagel
6. 4.5% w/v α-cellulose, 0.75% w/v methyl cellulose, 0.1% w/v phytagel
7. 5% w/v α-cellulose, 0.75% w/v methyl cellulose, 0.1% w/v phytagel

29

Results

Addition of 0.75%-1.0% w/v. methylcellulose in combination with 0.1%-0.2% w/v phytagel plus 4-4.5% w/v α-cellulose improved the consistency of nutrient medium (i.e. prevented gel separation and provided smooth texture) (Table 5.3).

It is possible to store medium with methylcellulose for at least 4 to 7 days without the occurrence of gel separation or clumping. The medium should be stored at 4° C. to prevent microbial growth. As antibiotics in solution do not remain stable for more than 3 days, it is recommended to add antibiotics to medium just prior to use after the storage period.

The addition of 0.75%-1.0% w/v methylcellulose in combination with 0.1%-0.2% w/v phytagel and 4-4.5% w/v α-cellulose improved the consistency of the nutrient medium in the miniplug cells. The addition of methylcellulose also allowed for storage for 4-7 days at 4° C. (if heat-sensitive components were added just prior to use). It is preferable to incorporate 0.8% w/v methylcellulose with 0.2% w/v phytagel+4.5% w/v α-cellulose in the nutrient medium.

rm8GMD macro nutrients, micro nutrients and vitamins, amino acids (see Example 5), 3% w/v sucrose, 0.1 μM IBA, 0.05 μM BA, Benlate (0.1 g/l), Ampicillin (0.1 g/l), 4.5% w/v alpha cellulose, 0.8% w/v methylcellulose and 0.2% w/v phytagel. Note that the medium volume was adjusted to accommodate the fact that 1 g of alpha cellulose occupied 1 ml of medium. To sow germinants, the root radicle of the germinants was inserted into the medium by hand. For each of the twelve genotypes, between 100 and 250 germinants were planted (in 2 to 5 replicates of 50 germinants).

Prior to sowing and nutrient medium dispensing, miniblocks and rooting sponges were sanitized by applying hot water so that the rooting sponge reached a temperature of 65° C. Miniblocks were then leached with plain water to lower EC levels in blocks. The miniblocks were then fertilized with 11-41-8, NPK at 50 ppm nitrogen.

After sowing, the miniplug trays were placed in a greenhouse with similar environmental conditions, fertility and pesticide regimes as described in Example 4, except germinants were not maintained in horticultural chambers for any of the growth period. Instead, germinants were only transitioned through greenhouse environments.

TABLE 5.3

Evaluation of nutrient medium consistency

| Treatments | Consistency with storage (4° C. and/or room temp.) | Comments on consistency in the miniblock cells. |
|---|---|---|
| 1. 4.5% w/v α-cellulose, no methyl cellulose 0.2% w/v phytagel | Gel separates with overnight storage and medium clumps | Runny as compared to media with methyl cellulose. The liquid components with dissolved nutrients and sugars seep out of α-cellulose matrix into and through miniplugs. This causes the bottom of blocks to be sticky with nutrients and promotes microbial growth on the bottom of blocks. |
| 2. 4.5% w/v α-cellulose, 1% w/v methyl cellulose, 0.1% w/v phytagel | Gel does not separate with storage and medium is smooth | Dispenses well into the cells. Structure maintained over a one week period. |
| 3. 5% w/v α-cellulose, 1% w/v methyl cellulose, 0.1% w/v phytagel | Gel does not separate with storage and medium is smooth | Dispenses well into the cells. Structure maintained over a one week period. |
| 4. 4.5% w/v α-cellulose, 1% w/v methyl cellulose, 0.2% w/v phytagel | Gel does not separate with storage and medium is smooth | Dispenses well into the cells. Structure maintained over a one week period. |
| 5. 5% w/v α-cellulose, 1% w/v methyl cellulose, 0.2% w/v phytagel | Gel does not separate with storage and medium is smooth | Dispenses well into the cells. Structure maintained over a one week period. |
| 6. 4.5% w/v α-cellulose, 0.75% w/v methyl cellulose, 0.1% w/v phytagel | Gel does not separate with storage and medium is smooth | Dispenses well into the cells. Structure maintained over a one week period. Reduced amount of methyl cellulose maybe better for automated dispensing |
| 7. 5% w/v α-cellulose, 0.75% w/v methyl cellulose, 0.1% w/v phytagel | Gel does not separate with storage and medium is smooth | Dispenses well into the cells. Structure maintained over a one week period. Reduced amount of methyl cellulose maybe better for automated dispensing |

EXAMPLE 6

The purpose of this experiment was to assess the performance of loblolly pine germinants in nutrient medium containing a combination of methylcellulose and α-cellulose. In addition, this trial provides a measure of conversion rates of germinants for twelve loblolly pine genotypes grown ex vitro in nutrient medium.

Methods

Somatic embryos of loblolly pine (genotypes LP 2-13) were pre-germinated using conventional in vitro medium and culture conditions. Germinants were then sown ex vitro into miniplugs containing 0.4 ml of nutrient medium. The medium employed consisted of the following ingredients:

Conversion percentage and morphological development of germinants were determined after 12 weeks growth ex vitro. A converted seedling was defined as a seedling that had a shoot height of between 2.5 and 5.0 cm and had a root system that was well developed throughout the rooting sponge.

Results

The modified nutrient medium (i.e., modified to include 0.8% w/v methylcellulose with 0.2% w/v phytagel and 4.5% w/v α-cellulose) was suitable for converting young loblolly pine somatic germinants into shippable miniplug seedlings. Nursery conversion rates ranged from 55% to 89% for individual genotypes (Table 6.1). The average conversion rate was 67% for all genotypes. Trial results showed that somatic germinants from a range of loblolly pine genotypes, could be planted into nutrient medium, and grown under non-sterile nursery conditions to yield commercially viable conversion rates.

TABLE 6.1

Conversion rate of loblolly pine germinants into shippable miniplug seedlings when grown with nutrient medium under standard (non-sterile) greenhouse conditions

| Genotype | Mean | SE |
|---|---|---|
| LP 2 | 55 | 5 |
| LP 3 | 70 | 7 |
| LP 4 | 57.5 | 9.5 |
| LP 5 | 55 | 0 |
| LP 6 | 70 | 10 |
| LP 7 | 89 | 5 |
| LP 8 | 74 | 1 |
| LP 9 | 68 | 0 |
| LP 10 | 60 | 2 |
| LP 11 | 72.5 | 2.5 |
| LP 12 | 74 | 1 |
| LP 13 | 61 | 1 |
| OVERALL: | 67 | |

EXAMPLE 7

The purpose of this example was to test the structural integrity of nutrient medium in miniplugs, particularly when milled peat and/or other soil mix components were used to replace α-cellulose in nutrient medium.

Methods

Standard nutrient medium consisted of the following ingredients: rm8GMD macro nutrients, micro nutrients and vitamins, amino acids (see Example 5), 3% w/v sucrose, 0.1 µM IBA, 0.05 µM BA, Benlate (0.1 g/l), Ampicillin (0.1 g/l), 0.8% w/v methylcellulose and 0.2% w/v phytagel. Apart from methylcellulose and phytagel, other structural components used (i.e. α-cellulose or peat and/or other soil mix components) are described in Table 8.1. Non-heat sensitive components of nutrient medium treatments were autoclaved 15 to 20 minutes for sanitization. Heat sensitive ingredients (including vitamins B5 and B12, amino acids, IBA, BA, Benlate, Ampicillin, and methylcellulose) were added after autoclaving. Note that the medium volume was adjusted to accommodate the fact that 1 g of alpha cellulose/1 g peat occupied 1 ml of medium. Medium volume was not adjusted to accommodate bentonite, vermiculite or perlite.

Media treatments (with structural components described in Table 7.1) were dispensed into separate 400-well miniplug blocks. One complete miniplug block was used per each treatment tested. Each miniplug received a 0.4 ml aliquot of medium treatment. Blocks were then placed in a greenhouse environment and subjected to a watering schedule in which blocks were watered once a day for 10 days and twice a day for 5 days. This simulated a normal twelve-week watering schedule in a greenhouse environment where blocks are usually subjected to 20 irrigations. Blocks were checked up to 3 times per week for 3 weeks to determine whether certain media treatments were better able to maintain structural integrity as compared to others (i.e. % plugs with sunken media were recorded).

TABLE 7.1

Nutrient medium treatments tested for structural integrity.

| Treatment | % α-cellulose (w/v) | % Peat (w/v) | % Vermiculite (w/v) | % Perlite (w/v) | % Bentonite (w/v) |
|---|---|---|---|---|---|
| 1 (control - SOP) | 4.5 | — | — | — | — |
| 2 | — | 5 | — | — | — |
| 3 | — | 5 | 1 | — | — |
| 4 | — | 5 | — | 1 | — |
| 5 | — | 5 | — | — | 3 |
| 6 | — | 5 | 1 | — | 1 |
| 7 | — | 5 | 0.5 | — | 2 |
| 8 | — | 5 | — | 1 | 1 |
| 9 | — | 5 | — | 0.5 | 2 |
| 10 | — | 5 | 0.5 | 0.5 | 1 |
| 11 | — | 4 | 1 | 1 | 2 |

Results

Standard nutrient medium containing 4.5% w/v α-cellulose: no sinking of the medium in 34% of the cavities (Table 7.2).

Nutrient medium containing a combination of 5% w/v peat and 3% w/v bentonite clay: no sinking of the medium in 98% of the cavities.

Nutrient medium containing any combination of peat and bentonite clay as part of the mix: no sinking of the medium in >80% of the cavities.

Replacing α-cellulose with a combination of peat and bentonite clay in the nutrient medium retained the structural integrity of nutrient medium throughout the time period tested, and supported seedlings grown in the nursery.

TABLE 7.2

Response of treatments with nutrient medium to the volume of water they would receive over a typical 12 week growing regime.

| Treatment | % Structural Integrity Material | | | | | | Plugs with Sunken Gem after Period in Greenhouse (GH) | | | | | | | %-Plugs with Sunken nutrient medium | |
|---|---|---|---|---|---|---|---|---|---|---|---|---|---|---|---|
| | α-Cellulose | Peat | Vermiculite | Perlite | Bentonite | No. of Plugs | 3 days in GH | 5 days in GH | 8 days in GH | 10 days in GH | 12 days in GH | 15 days in GH | 16 days in GH | % Sunken | % Not Sunken |
| 1 | 4.5 | — | — | — | — | 400 | 21 | 30 | 51 | 122 | 181 | 229 | 263 | 66 | 34 |
| 2 | — | 5 | — | — | — | 400 | 0 | 25 | 57 | 72 | 112 | 112 | 175 | 44 | 56 |
| 3 | — | 5 | 1 | — | — | 400 | 4 | 4 | 11 | 24 | 39 | 60 | 88 | 22 | 78 |
| 4 | — | 5 | — | 1 | — | 400 | 4 | 5 | 30 | 69 | 106 | 182 | 242 | 61 | 40 |
| 5 | — | 5 | — | — | 3 | 400 | 0 | 0 | 0 | 0 | 0 | 7 | 9 | 2 | 98 |
| 6 | — | 5 | 1 | — | 1 | 400 | 2 | 2 | 20 | 20 | 26 | 59 | 166 | 42 | 59 |
| 7 | — | 5 | 0.5 | — | 2 | 400 | 1 | 2 | 4 | 13 | 13 | 35 | 52 | 13 | 87 |
| 8 | — | 5 | — | 1 | 1 | 400 | 1 | 1 | 8 | 20 | 22 | 76 | 88 | 22 | 78 |
| 9 | — | 5 | — | 0.5 | 2 | 400 | 3 | 4 | 12 | 42 | 57 | 71 | 71 | 18 | 82 |

TABLE 7.2-continued

Response of treatments with nutrient medium to the volume of water they would receive over a typical 12 week growing regime.

| | % Structural Integrity Material | | | | | | Plugs with Sunken Gem after Period in Greenhouse (GH) | | | | | | | %-Plugs with Sunken nutrient medium | |
|---|---|---|---|---|---|---|---|---|---|---|---|---|---|---|---|
| Treatment | α-Cellulose | Peat | Vermiculite | Perlite | Bentonite | No. of Plugs | 3 days in GH | 5 days in GH | 8 days in GH | 10 days in GH | 12 days in GH | 15 days in GH | 16 days in GH | % Sunken | % Not Sunken |
| 10 | — | 5 | 0.5 | 0.5 | 1 | 400 | 4 | 4 | 23 | 61 | 94 | 123 | 169 | 42 | 58 |
| 11 | — | 4 | 1 | 1 | 2 | 400 | 0 | 0 | 2 | 4 | 6 | 28 | 41 | 11 | 89 |

EXAMPLE 8

The purpose of this example was to test the effects of using milled peat and/or other soil mix components to replace α-cellulose in nutrient medium while noting the effects on medium stability in miniplugs. In addition, this study tested the effects of using milled peat and/or other soil mix components in nutrient medium on loblolly pine germinant growth ex vitro.

Methods

Desiccated, mature loblolly pine embryos (genotype LP 11) were cultured on semi-solid medium for 7 days and then cultured in a liquid medium for 5 days using methods similar to those described in Example 1. At the end of priming, germinants were sown in miniplugs with 0.4 ml of nutrient medium with different structural components (Table 8.1). A total of 200 to 300 germinants were sown per each treatment (in 2 to 3 replicates of 100 germinants).

The standard nutrient medium consisted of the following ingredients: rm8GMD macro nutrients, micro nutrients and vitamins, amino acids (see Example 5), 3% w/v sucrose, 0.1 μM IBA, 0.05 μM BA, Benlate (0.1 g/l), Ampicillin (0.1 g/l), 0.8% w/v methylcellulose and 0.2% w/v phytagel. Apart from methylcellulose and phytagel, other structural components used (i.e. α-cellulose or peat and/or other soil mix components) are described in Table 8.1. Note that the medium volume was adjusted to accommodate the fact that 1 g of alpha cellulose/1 g peat occupied 1 ml of medium. Medium volume was not adjusted to accommodate bentonite, vermiculite or perlite. Non-heat sensitive components of nutrient medium treatments were autoclaved 15 to 20 minutes for sanitization. Heat sensitive ingredients (including vitamins B5 and B12, amino acids, IBA, BA, Benlate, Ampicillin, and methylcellulose) were added after autoclaving.

Germinants were grown under the standard nursery cultural regime (under greenhouse environmental conditions, and fertility and pesticide regimes described in Example 4), except germinants were not placed in a horticultural growth chamber for any period prior to growing germinants in the greenhouse. Instead, germinants were only transitioned through greenhouse environments. During the experiment, germinant survival and conversion rates were recorded every two weeks starting from the 2nd week of growth after sowing ex vitro per each treatment. Nutrient medium stability of the different treatments was also observed.

TABLE 8.1

Treatments for Nutrient Medium

| Treatment | % alpha cellulose (w/v) | % Peat (w/v) | % Vermiculite (w/v) | % Perlite (w/v) | % Bentonite (w/v) |
|---|---|---|---|---|---|
| 1 (control - SOP) | 4.5 | — | — | — | — |
| 2 | — | 5 | — | — | — |
| 3 | — | 5 | — | — | 1.5 |
| 4 | — | 5 | — | — | 3 |
| 5 | — | 5 | 0.5 | 1 | 2 |
| 6 | — | 5 | — | 0.5 | 2 |
| 7 | — | 4 | 1 | 1 | 2 |

Results

Survival and conversion data at 12 weeks of growth ex vitro showed that germinants sown in nutrient medium with 5% w/v peat with 1.5% w/v or 3% w/v bentonite clay had higher mean survival and conversion than other treatments (Table 8.2). Nutrient medium with 4% w/v peat, 1% w/v vermiculite, 1% w/v perlite and 2% w/v bentonite also had high survival and conversion rates. These treatments also provided long lasting stability to germinants in the miniplugs. It was observed that miniplugs with nutrient medium where α-cellulose was replaced with peat and 1.5% to 5% w/v clay did not show nutrient medium sinking into miniplugs during the 12-week culture period. Replacing α-cellulose with peat and other soil mix components can improve ex vitro germinant conversion as well as germinant stability in miniplugs. Improved conversion rates may result in part to the loss of fewer germinants due to their instability in miniplugs.

TABLE 8.2

%-Survival and %-conversion for germinants grown in nutrient medium with different structural components

| Treatment | % α-cellulose (w/v) | % Peat (w/v) | % Vermiculite (w/v) | % Perlite (w/v) | % Bentonite (w/v) | %-Survival ± SE | %-Conversion ± SE |
|---|---|---|---|---|---|---|---|
| 1 (control - SOP) | 4.5 | — | — | — | — | 55.0 ± 2.0 | 54.5 ± 2.5 |
| 2 | — | 5 | — | — | — | 56.3 ± 25.2 | 56.3 ± 25.2 |
| 3 | — | 5 | — | — | 1.5 | 76.3 ± 5.5 | 75.3 ± 5.2 |
| 4 | — | 5 | — | — | 3 | 77.7 ± 7.5 | 76.0 ± 7.8 |
| 5 | — | 5 | 0.5 | 1 | 2 | 51.3 ± 21.7 | 50.3 ± 21.2 |

TABLE 8.2-continued

%-Survival and %-conversion for germinants grown in
nutrient medium with different structural components

| Treatment | % α-cellulose (w/v) | % Peat (w/v) | % Vermiculite (w/v) | % Perlite (w/v) | % Bentonite (w/v) | %-Survival ± SE | %-Conversion ± SE |
|---|---|---|---|---|---|---|---|
| 6 | — | 5 | — | 0.5 | 2 | 47.5 ± 26.5 | 47.5 ± 26.5 |
| 7 | — | 4 | 1 | 1 | 2 | 75.5 ± 8.5 | 73.5 ± 7.5 |

EXAMPLE 9

Nutrient medium is required for survival and conversion of conifer somatic embryos that are imbibed on semi-solid medium, primed in a liquid medium (as described in Example 1), and then sown ex vitro under high relative humidity conditions. This study was carried out to determine whether liquid-primed germinants could germinate at a relative humidity as low as 70%. In addition, this experiment compared the survival and conversion of germinants sown in polymerized peat plugs containing nutrient medium with and without sucrose or structural support.

Methods

Fresh, mature loblolly pine embryos (genotype LP 14) were stored on high relative humidity treatment (HRHT) plates and subsequently cultured on semi-solid medium for 7 days and then cultured in a liquid medium for 5 days using methods similar to those described in Example 1. At the end of the liquid culture step, germinants were sown in miniplugs with 0.4 ml of different treatments of nutrient medium (Table 9.1). Four replicates of 50 germinants were sown for each treatment. The standard nutrient medium consisted of the following ingredients: rm8GMD macro nutrients, micro nutrients and vitamins, amino acids (see Example 5), 3% w/v sucrose, 0.1 µM IBA, 0.05 µM BA, Benlate (0.1 g/l), Ampicillin (0.1 g/l), 0.8% w/v methylcellulose, 4.5% w/v α-cellulose and 0.2% w/v phytagel. Note that the medium volume was adjusted to accommodate the fact that 1 g of alpha cellulose occupied 1 ml of medium.

After sowing, germinants were monitored every second week for survival. In addition, conversion was monitored every second week, starting from the $4^{th}$ week of ex vitro growth until 12 weeks of growth in the nursery.

TABLE 9.1

Treatments

| Treatment | Ex vitro nutrient medium treatment | Relative Humidity |
|---|---|---|
| 1 (ex vitro SOP control) | Medium with 3% w/v sucrose | 95% RH 2 weeks (lab chamber), then transferred to Greenhouse Zone 1* |
| 2 | Medium with 3% w/v sucrose | 90% RH (lab chamber) |
| 3 | Medium with 0% sucrose | 90% RH (lab chamber) |
| 4 | Medium without phytagel, α-cellulose or methylcellulose | 90% RH (lab chamber) |
| 5 | Medium with 3% w/v sucrose | 80% RH (Greenhouse) |
| 6 | Medium with 3% w/v sucrose | 70% RH (HGC chamber) |

TABLE 9.1-continued

Treatments

*Greenhouse Zone 1 Environmental Conditions: Temperature - 22 to 16° C., Lighting - 150 to 300 µmol $m^{-2}s^{-1}$ PAR, Humidity - normally 92 to 85% RH, Fertigation - 11-41-8 at 50 ppm N, Pest control - same as Example 2

Results

Figure 6:
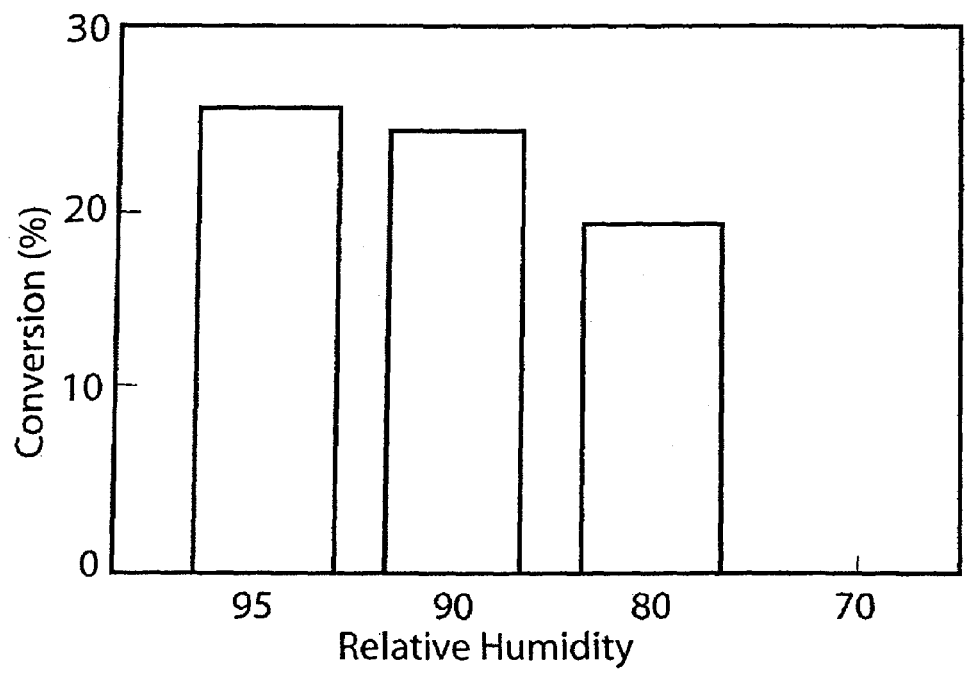
FIGS. 6 and 7 are graphs showing the results of tests carried out in the Examples below.

Conversion rates were highest where germinants were maintained in 90-95% RH. Germinant conversion rates declined as the relative humidity dropped to 80% RH. Germinants did not survive when maintained at 70% RH. FIG. 6 of the accompanying drawings is a graph showing the conversion rates of loblolly pine embryos that were exposed to a range of humidity values during ex vitro culture.

Figure 7:
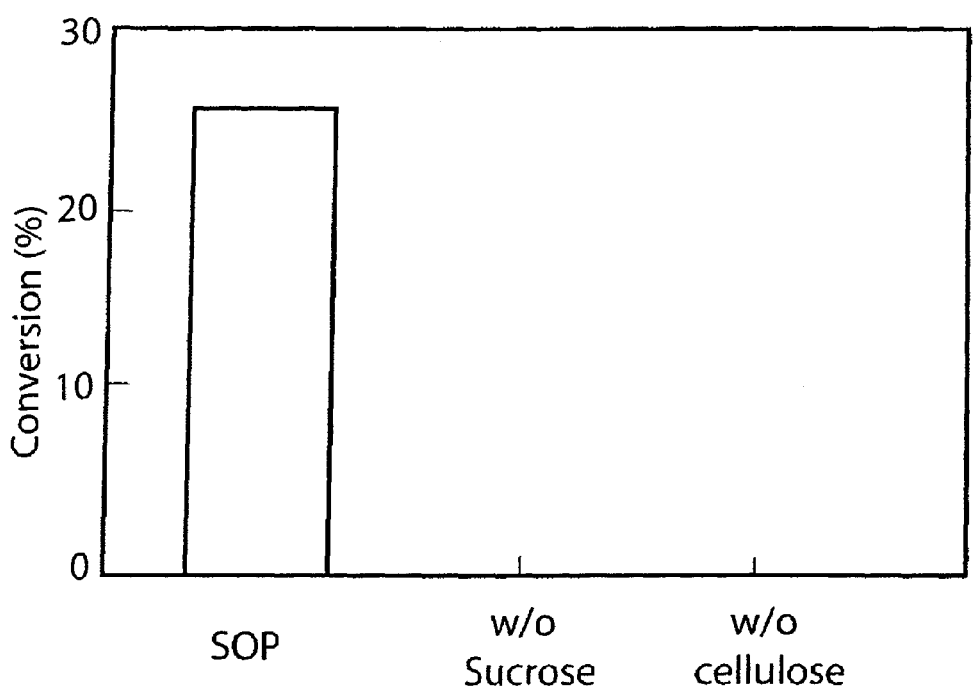

Germinants did not survive under ex vitro growing conditions when they were not supplied with sucrose in the nutrient media. Germinants did not survive under ex vitro growing conditions when not supplied with structural support in nutrient medium (i.e. α-cellulose, methylcellulose and phytagel). FIG. 7 is a graph showing the conversion rate of loblolly pine embryos under ex vitro conditions that were sown in nutrient medium with and without sucrose or structural support.

What we claim is:

1. A nutrient medium for a somatic plant embryo or germinant of a conifer species, which medium comprises particles of a solid component present within an aqueous flowable component comprising a flowable or semi-solid component containing a carbohydrate nutrient for the embryo or germinant, wherein said nutrient medium has a viscosity such that, when contacted with said embryo or germinant, at least some of said flowable or semi-solid component containing the carbohydrate nutrient remains in contact with said embryo or germinant as said embryo or germinant proceeds to grow and convert to an autotrophic seedling under environmental conditions effective for said conversion, and wherein said particles of the solid component of the nutrient medium remain in contact with said embryo or germinant after said flowable or semi-solid material dissipates, thereby providing continuing physical support for said embryo or germinant after said dissipation.

2. The medium of claim 1, which comprises employing, as said nutrient medium, a medium that has a fluidity under said environmental conditions such that it may be dispensed under gravity or pressure from an orifice onto said porous solid growth substrate.

3. The medium of claim 1, wherein said solid particles comprise flexible or elongated fibers.

4. The medium of claim 3, wherein said fibers are made of alpha-cellulose.

5. The medium of claim 4, wherein said fibres are present in a concentration range up to 10% (w/v).

6. The medium of claim 4, wherein said fibers are present in the range between 3 and 8% (w/v).

7. The medium of claim 4, wherein said medium also contains methyl-cellulose, agar, agarose, phytagel, gellan gum, or gelcarin either singly or in combinations of two or more of the aforementioned gelling agents.

8. The medium of claim 1, wherein said solid component comprises milled or sifted peat moss, perlite, vermiculite, clay, diatomaceous earth, coir, or silica either singly or with 2 or more of the aforementioned solid components combined.

9. The medium of claim 8, wherein said solid components are present, either singly or with two or more of the solid components used in combination, in a concentration range up to a total of 0.5 to 10% w/v.

10. The medium of claim 8, wherein said medium also contains methyl-cellulose, agar, agarose, phytagel, gellan gum, or gelcarin either singly or in combinations of two or more of the aforementioned gelling agents.

* * * * *